(12) United States Patent
Sauer

(10) Patent No.: US 11,311,285 B2
(45) Date of Patent: Apr. 26, 2022

(54) PROSTHETIC SUTURING DEVICE AND METHODS THEREOF

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 424 days.

(21) Appl. No.: 15/387,101

(22) Filed: Dec. 21, 2016

(65) Prior Publication Data

US 2017/0172564 A1   Jun. 22, 2017

Related U.S. Application Data

(60) Provisional application No. 62/270,472, filed on Dec. 21, 2015.

(51) Int. Cl.
*A61B 17/04*   (2006.01)
*A61F 2/24*   (2006.01)
*A61B 17/062*   (2006.01)

(52) U.S. Cl.
CPC ...... *A61B 17/0469* (2013.01); *A61B 17/0482* (2013.01); *A61B 17/0625* (2013.01); *A61F 2/2409* (2013.01); *A61B 2017/0472* (2013.01)

(58) Field of Classification Search
CPC ............ A61B 17/0469; A61B 17/0482; A61B 2017/0472; A61B 17/0625; A61B 17/0401; A61B 17/0483; A61B 17/0485; A61B 17/0491; A61B 17/0467; A61B 2017/0488; A61B 2017/049; A61B 2017/0496; A61B 2017/00371; A61F 2/2409
See application file for complete search history.

(56) References Cited

U.S. PATENT DOCUMENTS

| | | | |
|---|---|---|---|
| 3,996,623 A | 12/1976 | Kaster | |
| 5,431,666 A | 7/1995 | Sauer | |
| 5,520,702 A * | 5/1996 | Sauer | A61B 17/0469 |
| | | | 29/751 |
| 5,562,686 A | 10/1996 | Sauer | |
| 5,766,183 A | 6/1998 | Sauer | |

(Continued)

OTHER PUBLICATIONS

Oct. 3, 2009 Product Literature; LSI Solutions® Sew-Right SR.5™ Device and SR.5™ Quick Load™ Inservice Guide.

(Continued)

*Primary Examiner* — Tuan V Nguyen
*Assistant Examiner* — Chima U Igboko
(74) *Attorney, Agent, or Firm* — Michael E Coyne

(57) ABSTRACT

A prosthetic suturing device is disclosed. The prosthetic suturing device has a guide tip defining a cuff receiving area. The device also has a guide tip having at least one needle guide configured to guide at least one needle through the cuff receiving area. Another prosthetic suturing device is disclosed. The prosthetic suturing device has a guide tip defining a cuff receiving area and comprising first and second apertures for receiving a suture adapter. The prosthetic suturing device also has first and second needles, each needle having an end configured to engage a suture adapter. The prosthetic suturing device further has at least one set of needle guides configured to guide the first and second needles through the cuff receiving area. The prosthetic suturing device also has a grip pointing in a direction substantially orthogonal to the cuff receiving area.

9 Claims, 25 Drawing Sheets

(56) References Cited

U.S. PATENT DOCUMENTS

| | | | |
|---|---|---|---|
| 5,908,428 A | 6/1999 | Scirica | |
| 6,187,019 B1* | 2/2001 | Stefanchik | A61B 17/11 606/144 |
| 6,368,334 B1 | 4/2002 | Sauer | |
| 6,533,796 B1 | 3/2003 | Sauer | |
| 6,997,931 B2 | 2/2006 | Sauer | |
| 7,211,093 B2 | 5/2007 | Sauer | |
| 7,407,505 B2 | 8/2008 | Sauer | |
| 7,731,727 B2 | 6/2010 | Sauer | |
| 8,313,496 B2 | 11/2012 | Sauer | |
| 8,398,657 B2 | 3/2013 | Sauer | |
| 8,652,149 B2 | 2/2014 | Sauer | |
| 2002/0107530 A1 | 8/2002 | Sauer | |
| 2002/0120290 A1* | 8/2002 | Green | A61B 17/0057 606/213 |
| 2003/0236535 A1* | 12/2003 | Onuki | A61B 17/0469 606/144 |
| 2004/0068272 A1 | 4/2004 | Sauer | |
| 2005/0154402 A1* | 7/2005 | Sauer | A61B 17/0482 606/139 |
| 2005/0154403 A1 | 7/2005 | Sauer | |
| 2005/0165419 A1 | 7/2005 | Sauer | |
| 2005/0251153 A1* | 11/2005 | Sakamoto | A61B 17/0469 606/139 |
| 2007/0255296 A1 | 11/2007 | Sauer | |
| 2009/0222027 A1 | 9/2009 | Sauer | |
| 2010/0211083 A1 | 8/2010 | Sauer | |
| 2011/0118758 A1 | 5/2011 | Sauer | |
| 2012/0016383 A1 | 1/2012 | Sauer | |
| 2012/0029536 A1 | 2/2012 | Dicesare | |
| 2012/0053600 A1 | 3/2012 | Fortson | |
| 2015/0038800 A1 | 2/2015 | Prior et al. | |
| 2015/0133967 A1 | 5/2015 | Martin | |
| 2015/0282805 A1* | 10/2015 | Sauer | A61B 17/0469 606/145 |
| 2017/0172564 A1 | 6/2017 | Sauer | |

OTHER PUBLICATIONS

Jan. 1, 2003 Product Literature; LSI Solutions® Sew-Right SR.5™, the Single Squeeze Suturing Device™.

Jan. 1, 2007Product Literature; LSI Solutions® RD Technology Guide.

Product Literature; LSI Solutions® RD Running Device™ Surgery's Best Suturing Technology™.

Jun. 16, 2010 Symposium; Knight, Peter, for Presentation at the STS 2011 Annual Meeting-Automated Remote Transapical Wound Closure System: Fresh Porcine Heart Bursting Pressure Study and Cadaver Endoscopic Demonstration; See pages, in volume, from issue, as published by in.

Jun. 21, 2010 Symposium; Leigh, H., for Presentation at the STS 2011 Annual Meeting—Fresh Porcine Heart Bursting Pressure Study Fig. 1; See pages, in volume, from issue, as published by in.

Jan. 18, 2018 International Search Report; Thomas, Shane, International Search Report for PCT/US2017/057057.

Jun. 10, 2020 Foreign Search Report; Assion, Jean-Charles, European Search Report for EP17882961.

* cited by examiner

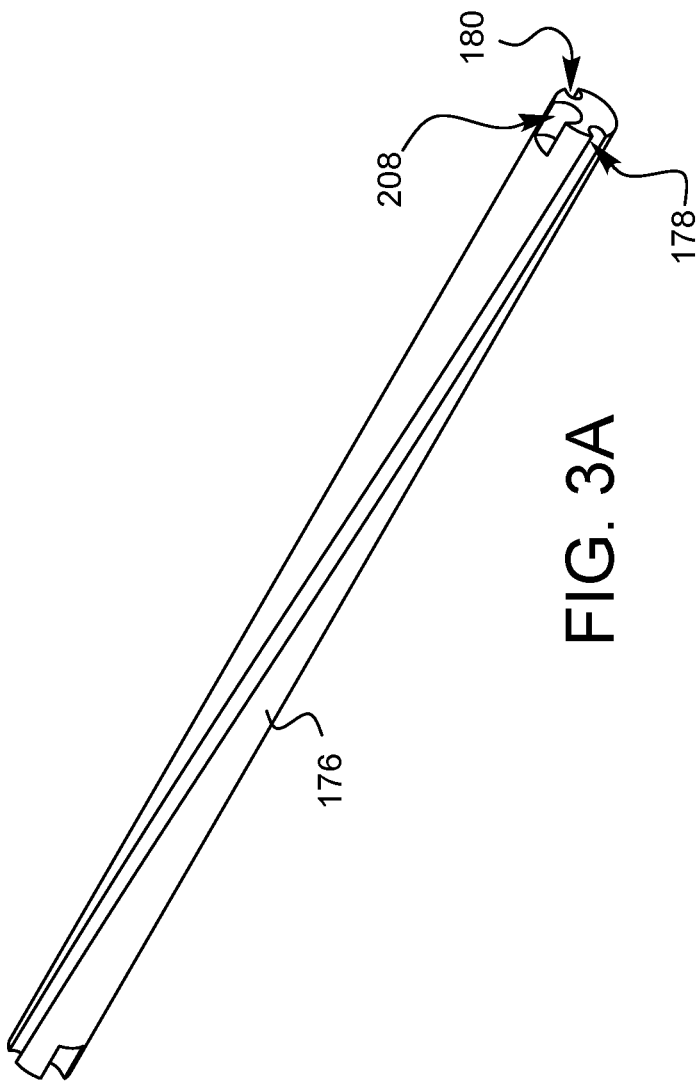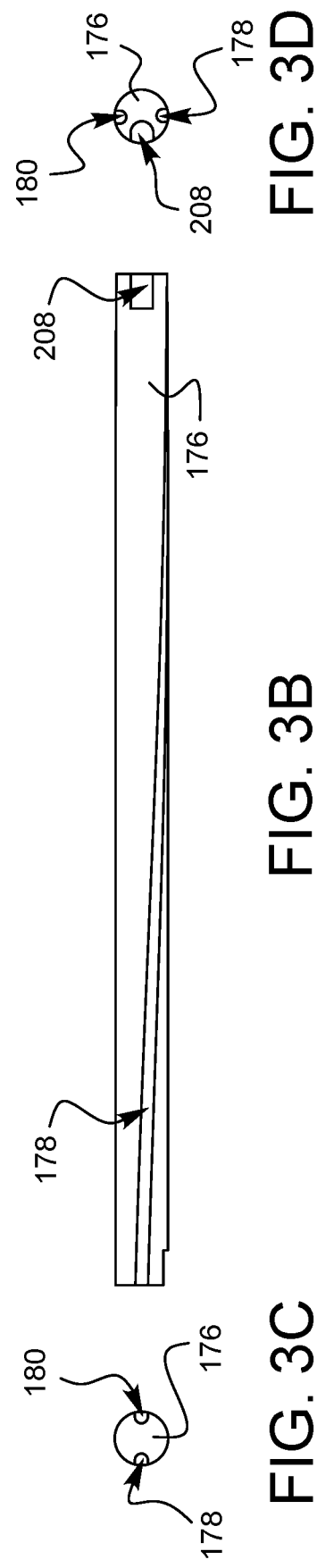

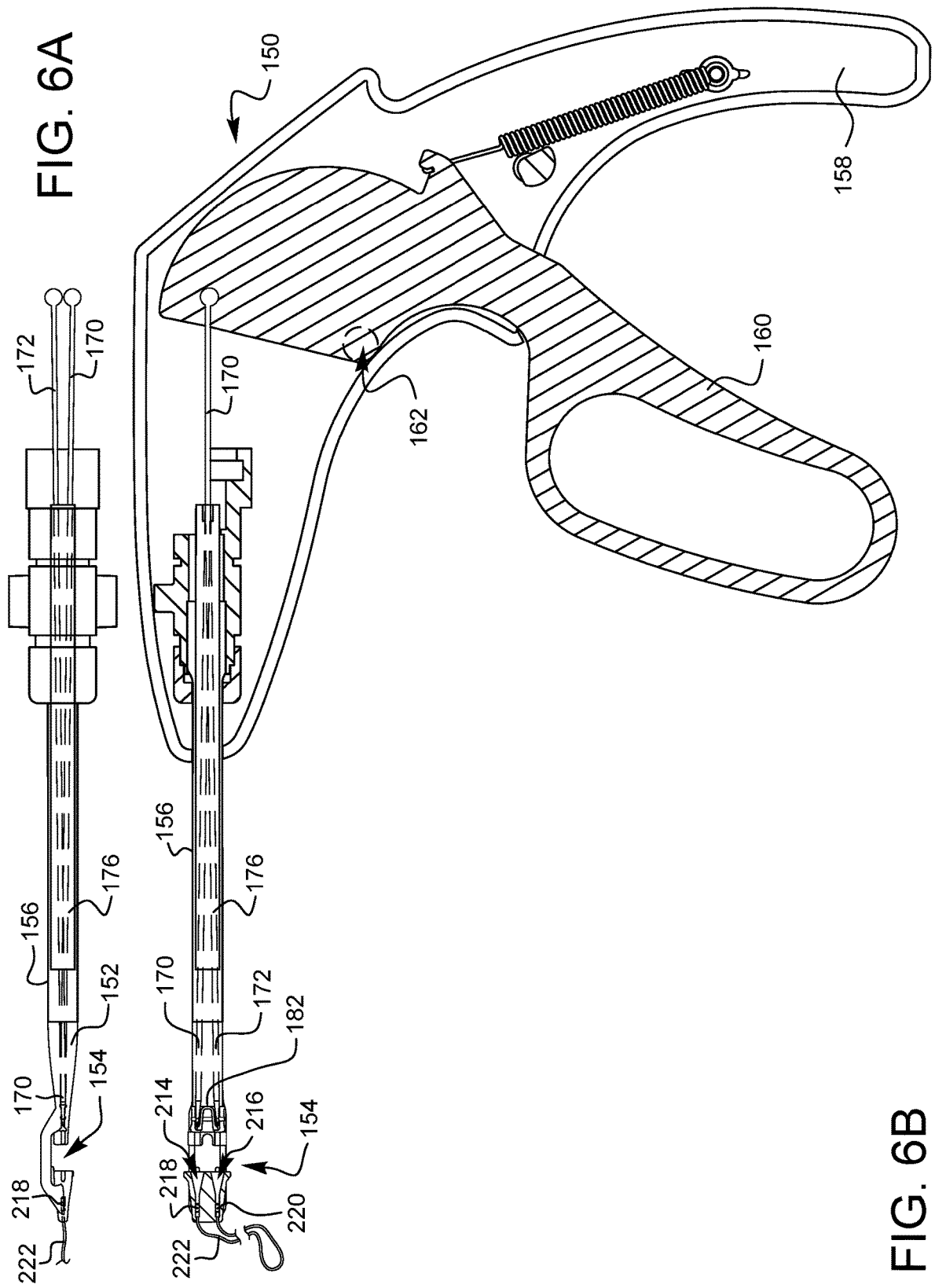

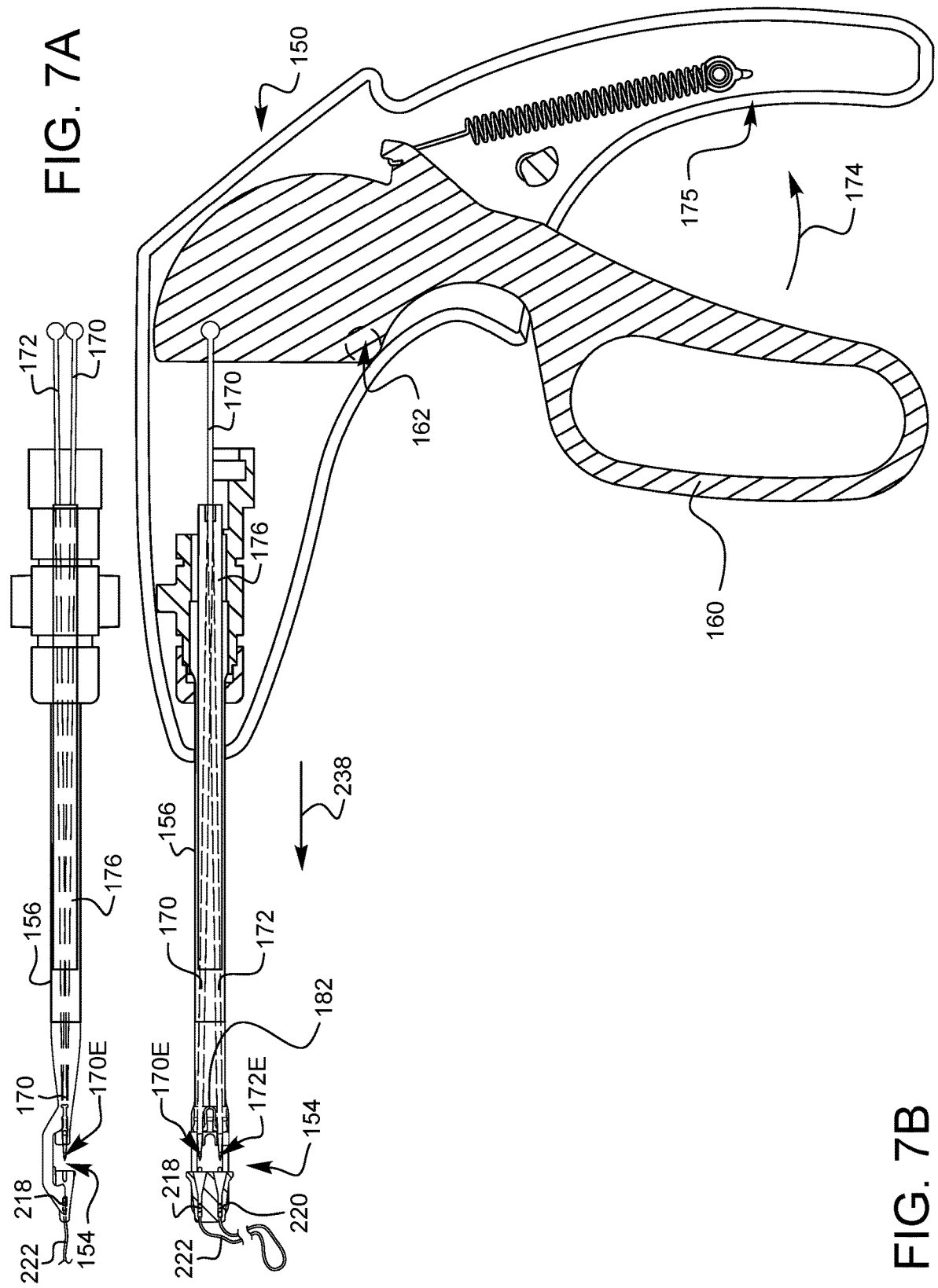

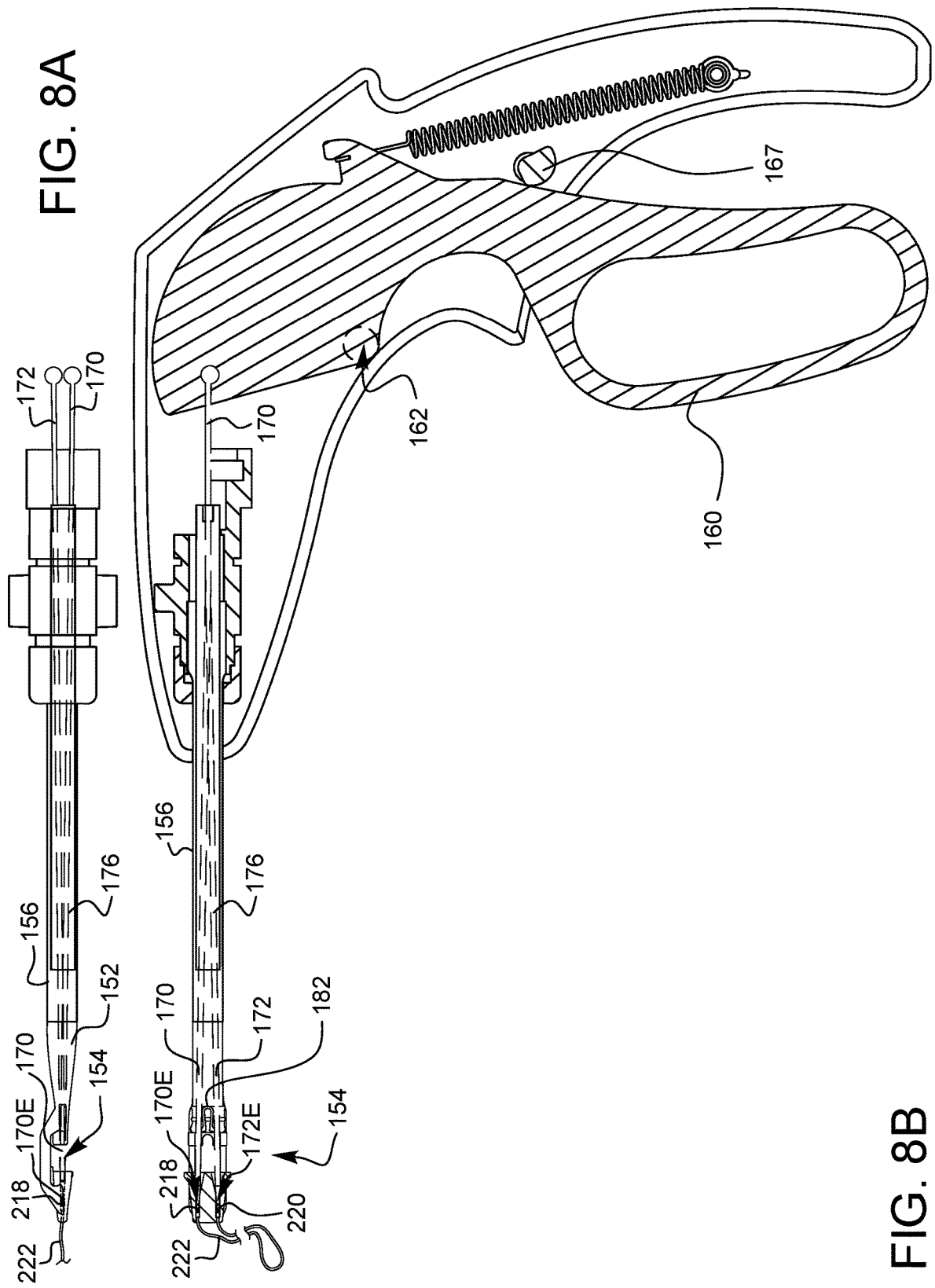

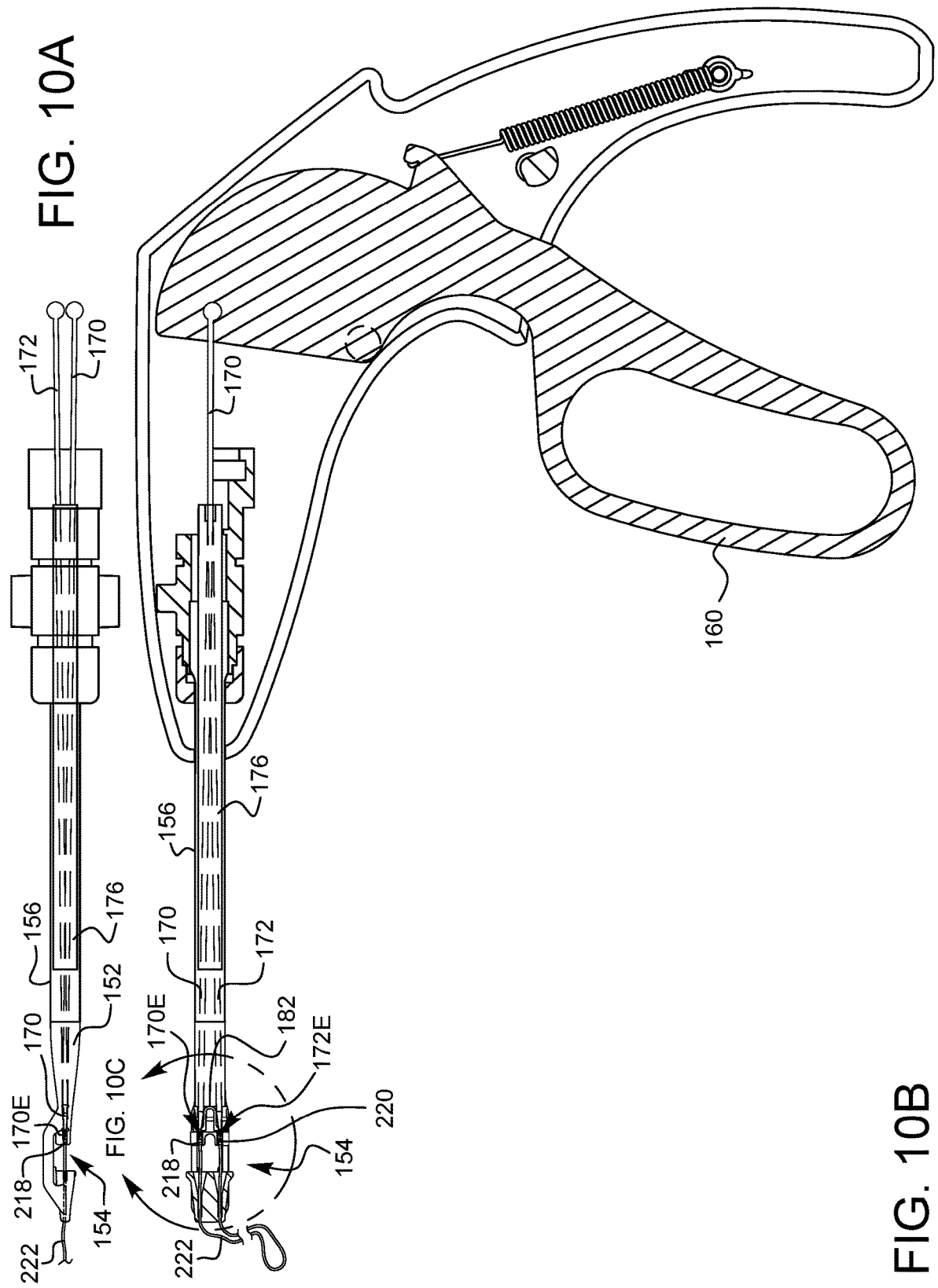

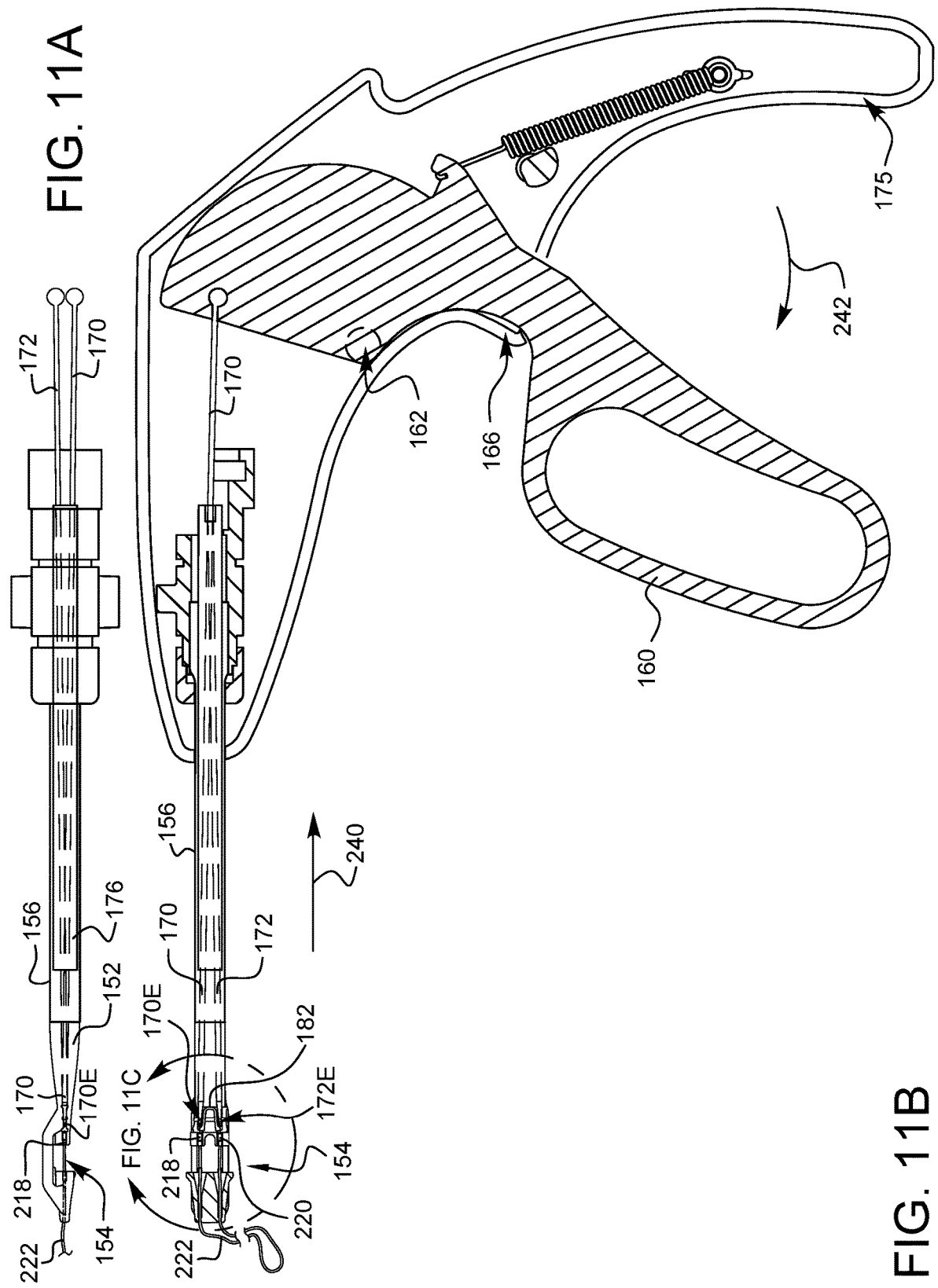

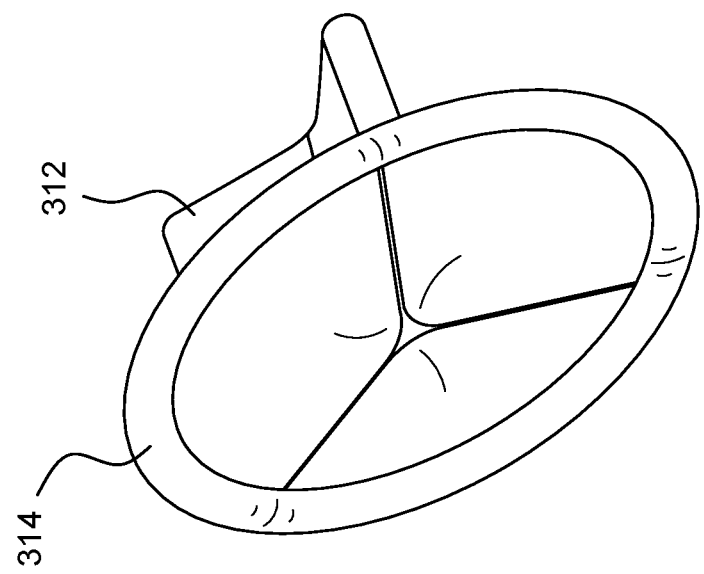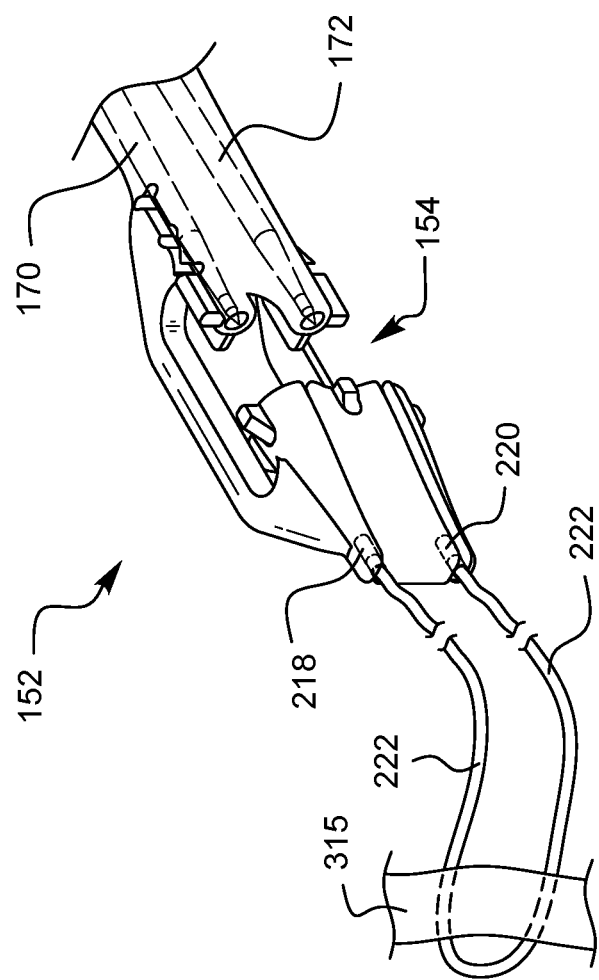
FIG. 18A

PROSTHETIC SUTURING DEVICE AND METHODS THEREOF

FIELD

The claimed invention relates to surgical suturing devices, and more specifically to surgical suturing devices suitable for use with prosthetic devices, especially cardiac prosthetic devices such as replacement heart valves.

BACKGROUND

Modern advances in cardiac surgery have made it possible to replace heart valves using minimally invasive surgical techniques. As minimally invasive techniques have improved, surgeons are able to operate on patients through smaller and smaller access holes, resulting in less perioperative pain and shorter recovery times. A main focus of innovations in minimally invasive cardiac surgery has been on the tools which pass into the patient, through the small access holes, to place suture stitches more efficiently and reliably. By focusing on improvements to these steps of the surgical procedures, patients are able to be on cardio-pulmonary bypass machines for shorter times, thereby improving patient outcomes. Resultant efficiency improvements while working within the patient further help to reduce stress and fatigue on surgeons.

It would also be advantageous to focus on efficiency outside of the patient. Surgical teams are regularly working to streamline their own processes to enable surgeons to be as efficient as possible. In many minimally invasive surgical procedures, the ends of sutures which have been stitched within a patient are brought back out of the patient through one of the access sites so that the suture ends can be kept organized and then stitched through a sewing ring of a prosthetic device. Unfortunately, the suture ends often have adapters which were previously used to enable a corresponding minimally invasive suturing device to manipulate the suture ends within the patient. While it might be possible to reload the adapters (and therefore the suture ends) into the minimally invasive suturing device, such devices (meant for in-patient use and suturing tissue) are often not compatible with suturing a sewing cuff of a prosthetic device. As a result, surgical teams are forced to cut off the adapters and thread each suture onto a needle in order to manually stitch each suture end through a prosthetic valve's sewing cuff. For many cardiac surgical procedures, unfortunately, this can increase the overall time a patient is on cardio-pulmonary bypass (CPB). Longer CPB times are associated with complications of the inflammatory system, heart, lungs, kidneys, and brain. Therefore, it would be desirable to have a prosthetic suturing device that is compatible with one or more suture adapters which have been used with a minimally invasive surgical suturing device and which has features to increase the efficiency of a surgical team and reduce CPB time.

SUMMARY

A prosthetic suturing device is disclosed. The prosthetic suturing device has a guide tip defining a cuff receiving area. The guide tip has at least one needle guide configured to guide at least one needle through the cuff receiving area.

Another prosthetic suturing device is disclosed. The prosthetic suturing device has a guide tip defining a cuff receiving area and comprising first and second apertures for receiving a suture adapter. The prosthetic suturing device also has first and second needles, each needle having an end configured to engage a suture adapter. The prosthetic suturing device further has at least one set of needle guides configured to guide the first and second needles through the cuff receiving area. The prosthetic suturing device also has a grip pointing in a direction substantially orthogonal to the cuff receiving area.

BRIEF DESCRIPTION OF THE DRAWINGS

FIG. 3A is an enlarged perspective view of one embodiment of a needle guide tube for a prosthetic suturing device.

FIGS. 3B, 3C, and 3D are side, back, and front elevational views, respectively, of the needle guide tube of FIG. 3A.

FIG. 6B is a partially cross-sectioned side view of the prosthetic suturing device of FIG. 1B with the needles in a retracted position.

FIG. 6A is a top view of the device from FIG. 6B, hiding the handle, housing, spring, and hard stop in order to more clearly show the proximal needle orientation.

FIG. 7B is a partially cross-sectioned side view of the prosthetic suturing device of FIG. 1B, with the needles in a partially engaged position as they pass through the cuff-receiving area.

FIG. 7A is a top view of the device from FIG. 7B, hiding the handle, housing, spring, and hard stop in order to more clearly shown the proximal needle orientation.

FIG. 8B is a partially cross-sectioned side view of the prosthetic suturing device of FIG. 1B, with the needles in a fully engaged position and coupled to the suture ferrules held in the distal end of the guide tip.

FIG. 8A is a top view of the device from FIG. 8B, hiding the handle, housing, spring, and hard stop in order to more clearly show the proximal needle orientation.

FIG. 10B is a partially cross-sectioned side view of the prosthetic suturing device of FIG. 1B, with the needles fully retracted.

FIG. 10A is a top view of the device from FIG. 10B, hiding the handle, housing, spring, and hard stop in order to more clearly show the proximal needle orientation.

FIG. 11B is a partially cross-sectioned side view of the prosthetic suturing device of FIG. 1B, with the needles hyper-retracted.

FIG. 11A is a top view of the device from FIG. 11B, hiding the handle, housing, spring, and hard stop in order to more clearly show the proximal needle orientation.

FIGS. 18A-18F illustrate one example of a surgical usage of an embodiment of a prosthetic suturing device.

Figure 1A:
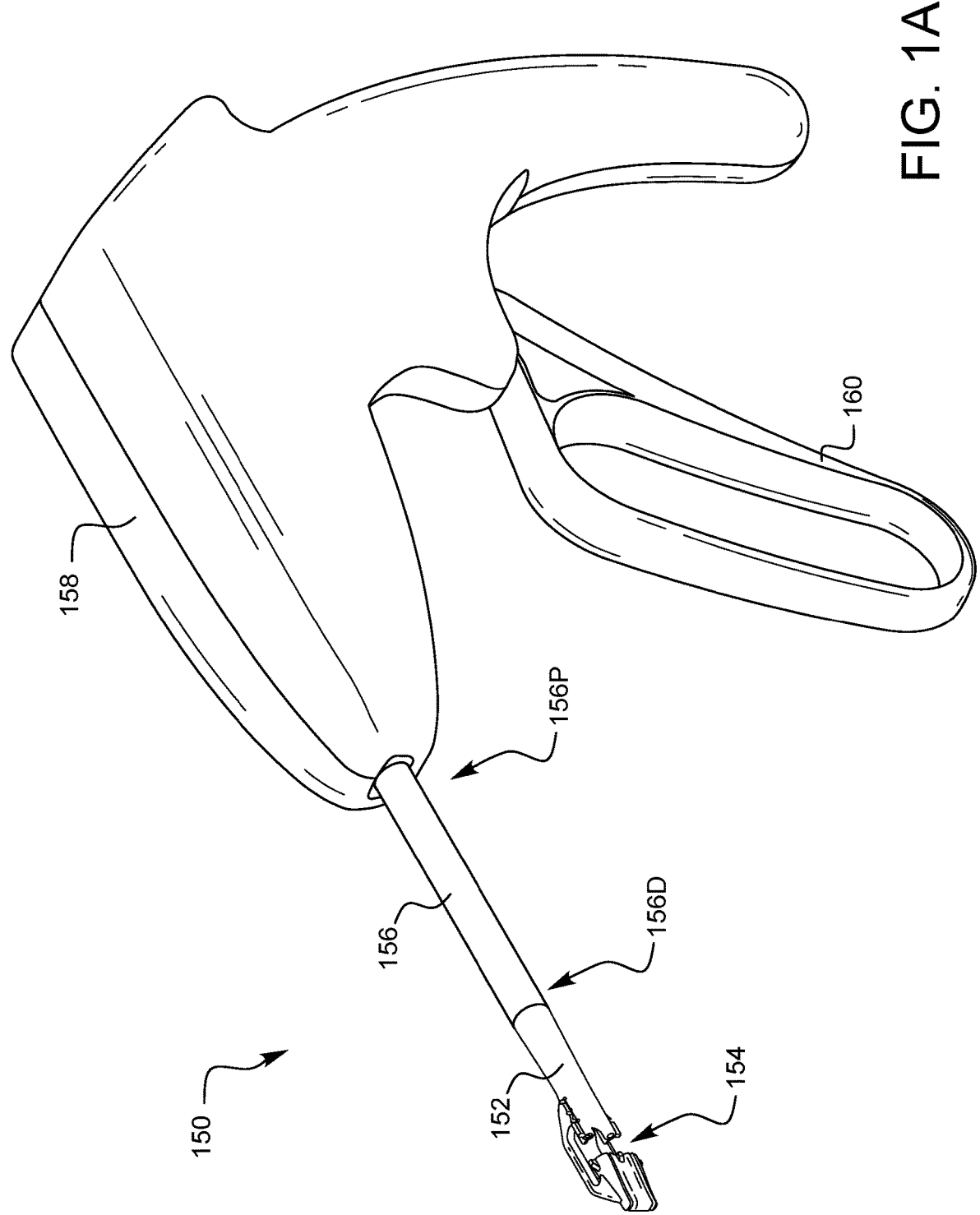
FIG. 1A is a perspective view of one embodiment of a prosthetic suturing device.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

Figure 1B:
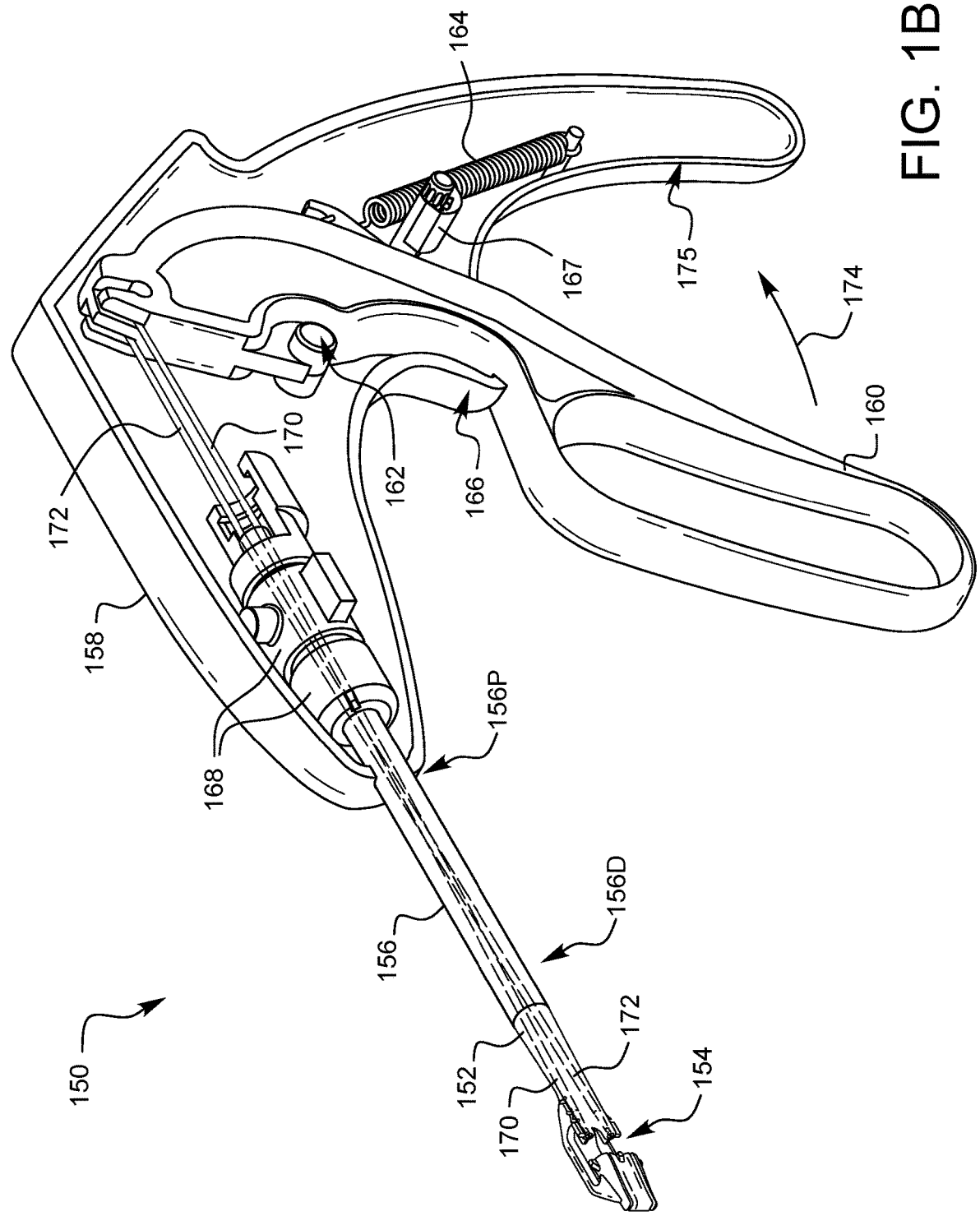
FIG. 1B is a partially exposed perspective view of the prosthetic suturing device of FIG. 1A with a portion of the housing removed.

FIG. 1A is a perspective view of one embodiment of a prosthetic suturing device 150. FIG. 1B is a partially exposed perspective view of the prosthetic suturing device 150 of FIG. 1A with a portion of the housing 158 removed. The prosthetic suturing device 150 has a guide tip 152 that defines a cuff receiving area 154. The cuff receiving area 154 is configured to receive a portion of a sewing cuff of a replacement anatomical structure. Examples of a replacement anatomical structure may include, but are not limited to, synthetic replacement heart valves and natural tissue replacement heart valves. The sewing cuff on such a replacement anatomical structure is designed to be sewn with suture against one or more tissue sites inside a patient so that the replacement anatomical structure is held in a desired location. It should be understood that the term "suture", as used herein, is intended to cover any thread, cable, wire, filament, strand, line, yarn, gut, or similar structure, whether natural and/or synthetic, in monofilament, composite filament, or multifilament form (whether braided, woven, twisted, or otherwise held together), as well as equivalents, substitutions, combinations, and pluralities thereof for such materials and structures. Furthermore, for convenience, this specification will often utilize the example of a sewing cuff on a replacement heart valve, however, it should be understood that other types of replacement anatomical structures are contemplated as well. Such replacement anatomical structures having sewing cuffs are known to those skilled in the art.

The guide tip 152 is coupled to a shaft 156 at a distal end 156D of the shaft 156. The prosthetic suturing device also has a housing 158 to which a handle 160 is pivotably coupled at pivot point 162. The handle 160 is biased by spring 164 towards a handle stop 166 which is formed from part of the housing 158. A hard stop 167 is also located in the housing 158, in order to limit the travel of the handle 160 when squeezed in a direction 174.

Shaft holders 168 couple a proximal end 156P of the shaft 156 to the housing 158. First and second needles 170, 172 are in horizontal alignment where they are coupled to the handle 160 within the housing 158. In this embodiment, the needles 170, 172 are routed by a needle guide tube (not visible in this view) so as to be in vertical alignment near the cuff-receiving area 154. Movement 174 of the portion of the handle 160 outside of the housing 158 towards the grip 175 of the housing 158 will move the needles 170, 172 across the cuff receiving area 154. Since the grip 175 is part of the housing 158, portions of this specification may indicate that certain components are coupled to the grip 175, which is accurate because the grip is part of the housing.

Figure 2:
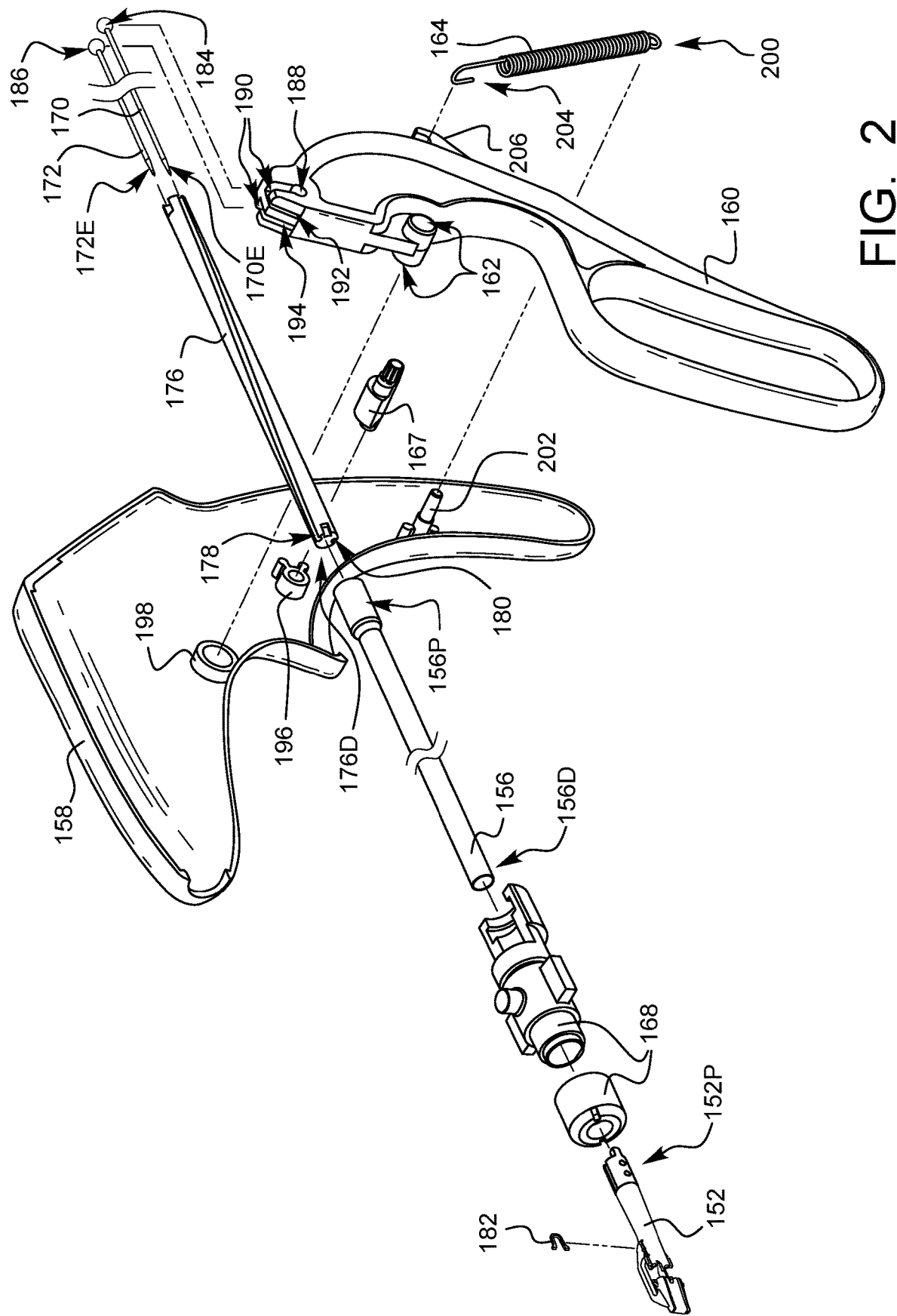
FIG. 2 is an exploded perspective view of the prosthetic suturing device of FIG. 1B.

FIG. 2 is an exploded perspective view of the prosthetic suturing device of FIG. 1B. The distal ends 170E, 172E of the first and second needles 170, 172 are each configured to engage a suture adapter (not shown here, but will be discussed later). A needle guide tube 176 having first and second spiral tracks 178, 180 is inserted into the proximal end 156P of the shaft 156, and shaft holders 168 are placed over the distal end 156D of the shaft 156 and coupled to the proximal end 156P of the shaft. The distal end 156D of the shaft 156 is coupled to the guide tip 152. A distal end 176D of the needle guide tube 176 abuts or lies close to a proximal portion 152P of the guide tip 152 inside a distal end 156D of the shaft 156. Starting with the needle ends 170E, 172E, the first and second needles 170, 172 are inserted into the first and second spiral tracks 178, 180 of the needle guide tube 176 as will be discussed below. The spiral tracks 178, 180 take the needles 170, 172 from a horizontal orientation to a vertical orientation at the proximal end of the device.

In the vertical orientation of the needles at the proximal end of the device, the second needle 172 will be located below the first needle 170. Before the first needle 170 is fully inserted, a ferrule release spring 182 may be inserted into a slot on the top of the guide tip 152 so that it rests against the second needle 172. Then, the first needle 170 can be fully inserted, compressing the ferrule release spring 182 between the two needles 170, 172.

A first ball end 184 is located on the proximal end of the first needle 170. Similarly, a second ball end 186 is located on the proximal end of the second needle 172. The second and first ball ends 186, 184 may be inserted into a side opening 188 in the handle 160. A top needle slot 190 allows the needles 170, 172 to move into the handle 160, and then the needles 170, 172 can be pivoted down into forward slots 192, 194, respectively, also formed in the handle 160. This couples the needles 170, 172 to the handle 160. The forward slots 192, 194 maintain the horizontal needle spacing at the proximal end of the device.

The pivot point 162 of the handle 160 may be aligned in a pivot boss 198 formed in the housing 158. The shaft holders 168 may be held and supported by a variety of features on the inside of the housing 158. Such features are not illustrated for simplicity, but are well known to those skilled in the art. Although only one half of the housing 158 is shown in this exploded view, it should be understood that a complementary half of the housing is also present (though not shown) and would have similar boss features to allow pivoting of the handle 160 and bracing of the shaft holders 168.

The hard stop 167 may be mounted in a hard stop boss 196 to limit travel of the handle 160, while a lower end 200 of spring 164 may be coupled to a fixed spring attachment point 202 on the housing. An upper end 204 of the spring 164 may be hooked onto a handle spring attachment point 206.

FIG. 3A is an enlarged perspective view of one embodiment of a needle guide tube 176 for a prosthetic suturing device. FIGS. 3B, 3C, and 3D are side, back, and front elevational views, respectively, of the needle guide tube 176 of FIG. 3A. In this embodiment, the needle guide tube 176 has a first spiral track 178 and a second spiral track 180. Looking at the back view of FIG. 3C, it can be seen that the spiral tracks 178, 180 will receive the first and second needles (not shown in this view) in a horizontal alignment from a proximal end of the device. Looking at the front view of FIG. 3D, it can be seen that the spiral tracks 178, 180 will have guided the needles into a vertical alignment near the guide tip (not shown in this view). The spiral tracks 178, 180 can provide support for a thinner needle so that the needles do not buckle when rotated to a different orientation. The needle guide tube 176 may also have a keyed portion 208 for mating with and/or aligning with a corresponding feature on the guide tip to ensure the needles exit the needle guide tube 176 and pass smoothly into the guide tip 152.

Figure 4:
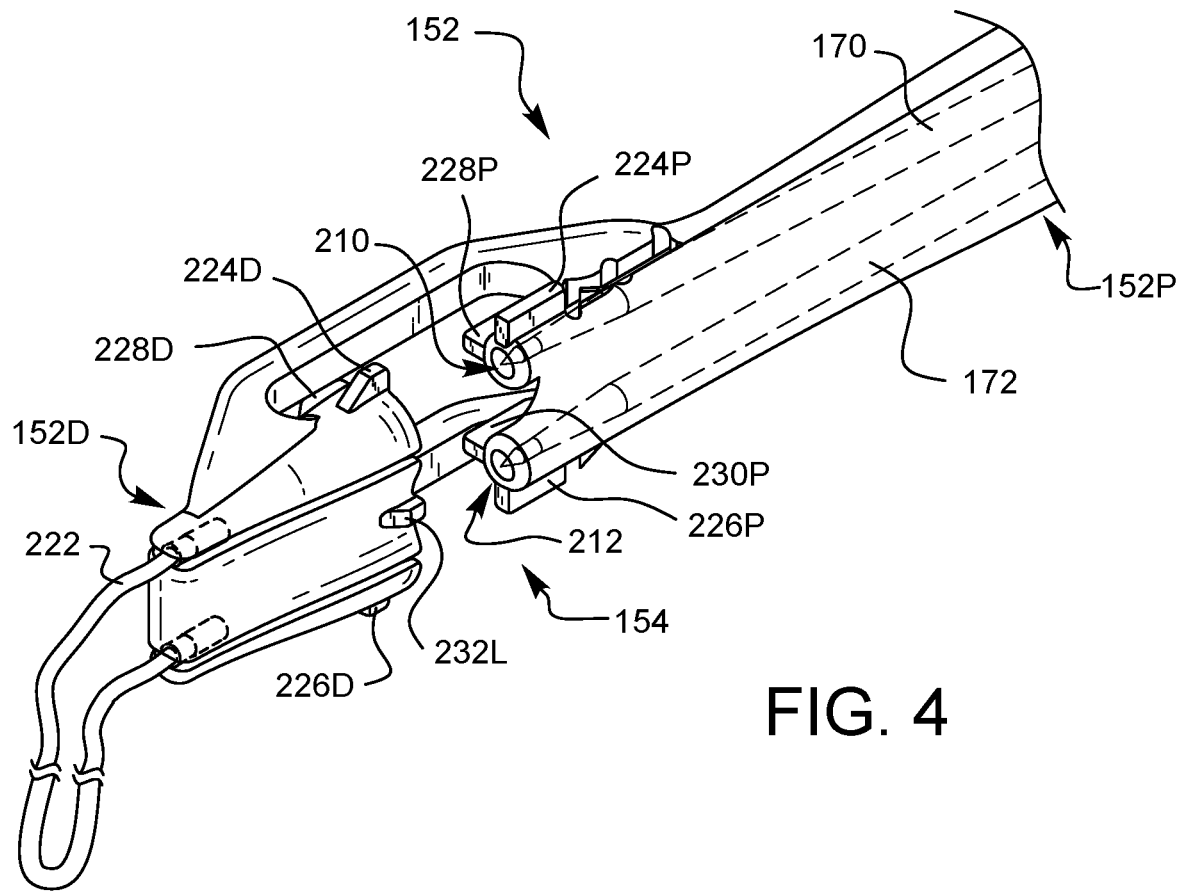
FIG. 4 is an enlarged perspective view of one embodiment of a guide tip for a prosthetic suturing device shown from a distal perspective.
Figure 5:
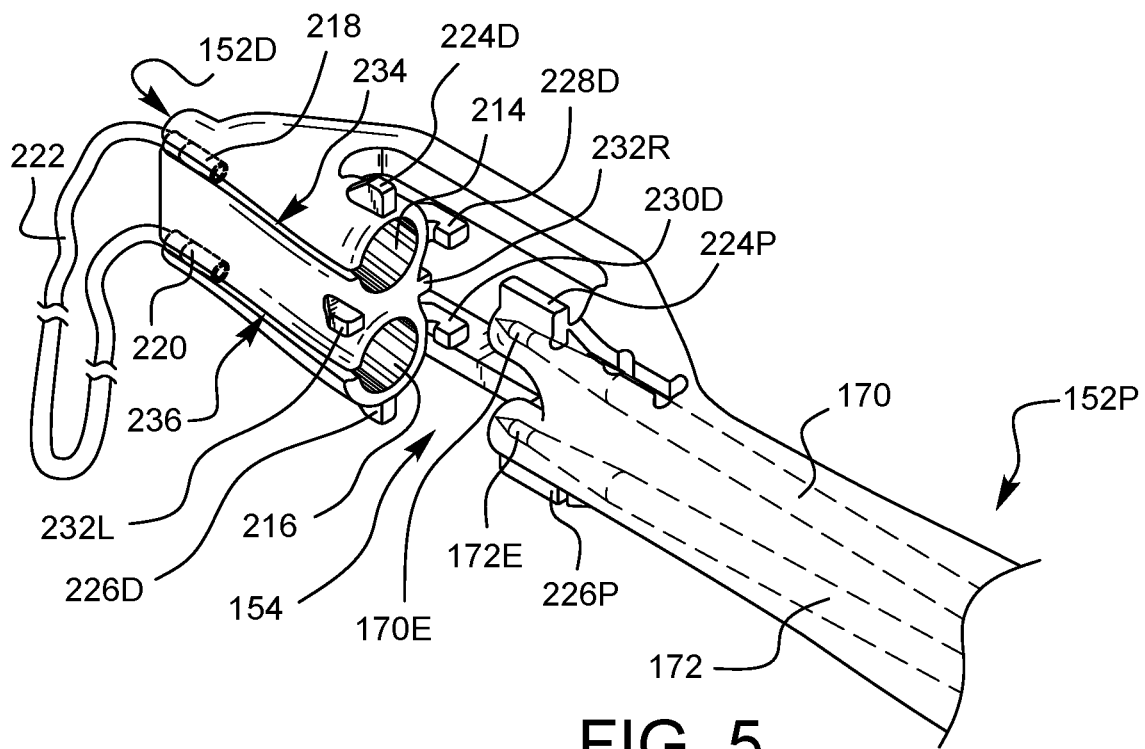
FIG. 5 is an enlarged perspective view of the guide tip from FIG. 4 shown from a proximal perspective.

FIGS. 4 and 5 are enlarged perspective views of one embodiment of a guide tip 152 for a prosthetic suturing device shown from distal and proximal perspectives, respectively. Passages pass within the proximal end 152P of the guide tip 152, guiding the first and second needles 170, 172 towards first and second needle guides 210, 212, respectively. The needle guides 210, 212 help to guide the needles 170, 172 through the cuff receiving area 154 defined by the guide tip 152.

The guide tip 152 also has first and second adapter receiving apertures 214, 216, located in the distal end 152D of the guide tip 152. The adapter receiving apertures 214, 216 are configured to hold first and second suture adapters 218, 220, respectively. The suture adapters 218, 220 may each be coupled to a different end of a suture 222. The suture adapters 218, 220 are designed to be engaged by the ends 170E, 172E of the first and second needles, respectively, such that the needles 170, 172, when contacting the adapters 218, 220 will be able to pull the adapters 218, 220 (and therefore, the ends of the suture 222) back through the cuff receiving area. One non-limiting example of suitable adapters include ferrules into which the needle tips 170E, 172E may be pressed. For convenience, this specification will refer to the adapters 218, 220 as ferrules. Similarly, the specification will also refer to the adapter receiving apertures 214, 216 as ferrule holders, but it should be understood that the broader interpretations apply where the claims are concerned, unless otherwise specified.

The distal end 152D of the guide tip 152 also defines first and second suture removal passages 234, 236 which are in communication with the first and second ferrule holders 214, 216. The removal passages 234, 236 allow the suture 222 which is coupled to the ferrules 218, 220 to be routed out the distal end 152D of the device after the ferrules 218, 220 are placed into the ferrule holders 214, 216.

The ferrule receiving apertures 214, 216 each have flared ends facing the cuff receiving area 154. As will be shown and discussed in more detail later in this specification, a sewing cuff of a replacement heart valve will be placed into the cuff receiving area, and then the needles 170, 172 will be advanced, piercing the sewing cuff and continuing on to couple with the ferrules 218, 220 before being withdrawn to pull the suture ends back through the sewing cuff. The sewing cuff material will tend to be pushed into the ferrule receiving apertures 214, 216, so the flared ends are helpful in preventing the sewing cuff material from becoming jammed between the needles 170, 172 and their respective ferrule receiving apertures 214, 216.

This embodiment of a guide tip 152 also has many different alignment guides for helping a user to visualize where the needles (which are mainly hidden from the user) will contact the sewing cuff. For example, the guide tip 152 has a first proximal horizontal needle alignment guide 224P adjacent the first needle guide 210. Similarly, the guide tip 152 has a second proximal horizontal needle alignment guide 226P adjacent the second needle guide 212. The guide tip 152 also has a first distal horizontal needle alignment guide 224D and a second distal horizontal needle alignment guide 226D adjacent the first and second ferrule receiving apertures 214, 216, respectively. As a sewing cuff is moved horizontally in relation to these horizontal needle alignment guides 224P, 224D, 226P, 226D, the intended horizontal penetration location of the needle relative the cuff can be judged from the alignment guides.

The guide tip 152 also has a first proximal vertical needle alignment guide 228P adjacent the first needle guide 210. Similarly, the guide tip 152 has a second proximal vertical needle alignment guide 230P adjacent the second needle guide 212. The guide tip 152 also has a first distal vertical needle alignment guide 228D and a second distal vertical needle alignment guide 230D adjacent the first and second ferrule receiving apertures 214, 216, respectively. As a sewing cuff is moved vertically in relation to these vertical needle alignment guides 228P, 228D, 230P, 230D, the intended vertical penetration location of the needle relative the cuff can be judged from the alignment guides.

The guide tip 152 also has a left central alignment guide 232L and a right central alignment guide 232R which are located on a plane substantially central to the first and second ferrule holders 214, 216 for further needle visualization.

FIG. 6B is a partially cross-sectioned side view of the prosthetic suturing device 150 of FIG. 1B with the needles 170, 172 in a retracted position. FIG. 6A is a top view of the device 150 from FIG. 6B, hiding the handle, housing, spring, and hard stop in order to more clearly show the proximal needle orientation. In this embodiment, on the proximal end, the needles 170, 172 are oriented in a horizontal row, but they are spiraled inside the device to be aligned to pass vertically into the cuff receiving area 154. In the retracted position of FIG. 6B, the ends of the needles 170, 172 are located just inside the guide tip 152 on the proximal side of the cuff receiving area 154.

FIG. 7B is a partially cross-sectioned side view of the prosthetic suturing device 150 of FIG. 1B, with the ends of the needles 170E, 172E in a partially engaged position as they pass through the cuff-receiving area 154. FIG. 7A is a top view of the device from FIG. 7B, hiding the handle, housing, spring, and hard stop in order to more clearly shown the proximal needle orientation. The handle 160 has been moved 174 toward the housing grip 175, causing the needles 170, 172 to be moved in a distal direction 238.

FIG. 8B is a partially cross-sectioned side view of the prosthetic suturing device 150 of FIG. 1B, with the ends of the needles 170E, 172E in a fully engaged position and coupled to the suture ferrules 218, 220 held in the distal end of the guide tip 152. FIG. 8A is a top view of the device from FIG. 8B, hiding the handle, housing, spring, and hard stop in order to more clearly show the proximal needle orientation. The handle 160 has contacted the hard stop 167 to prevent the needles 170E, 172E from pressing too hard into the ferrules 218, 220.

Figures 9A, 9B:
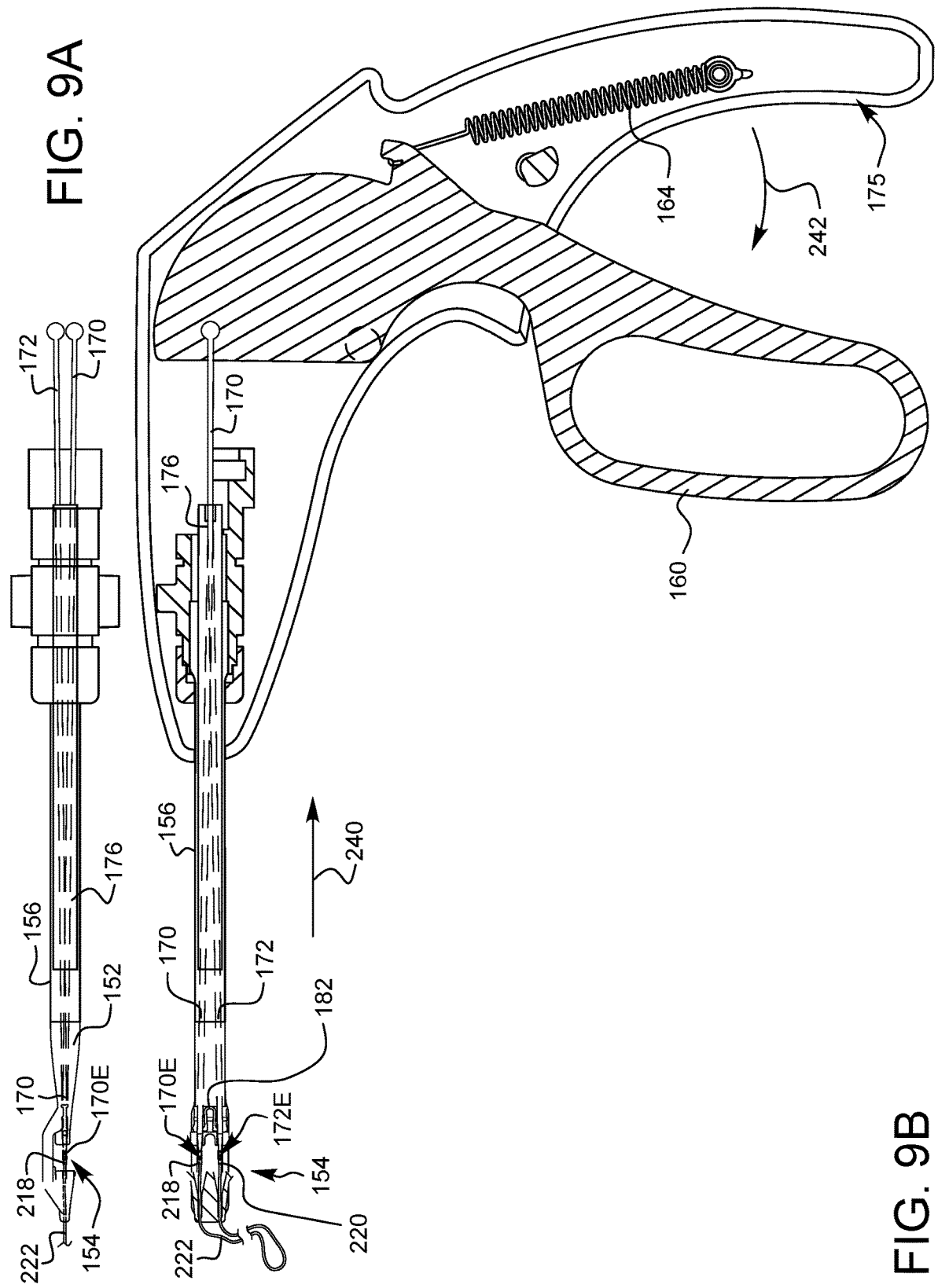
FIG. 9B is a partially cross-sectioned side view of the prosthetic suturing device of FIG. 1B, with the needles partially retracted and pulling the suture ferrules and suture back through the cuff receiving area.
FIG. 9A is a top view of the device from FIG. 9B, hiding the handle, housing, spring, and hard stop in order to more clearly show the proximal needle orientation.

FIG. 9B is a partially cross-sectioned side view of the prosthetic suturing device 150 of FIG. 1B, with the needles 170, 172 partially retracted and pulling the suture ferrules 218, 220 and suture 222 back through the cuff receiving area 154. FIG. 9A is a top view of the device from FIG. 9B, hiding the handle, housing, spring, and hard stop in order to more clearly show the proximal needle orientation. The handle 160 has been partially released, and the spring 164 has caused the handle to move 242 away from the housing grip 175, thereby causing the needles 170, 172 to move in a proximal direction 240.

Figure 10C:
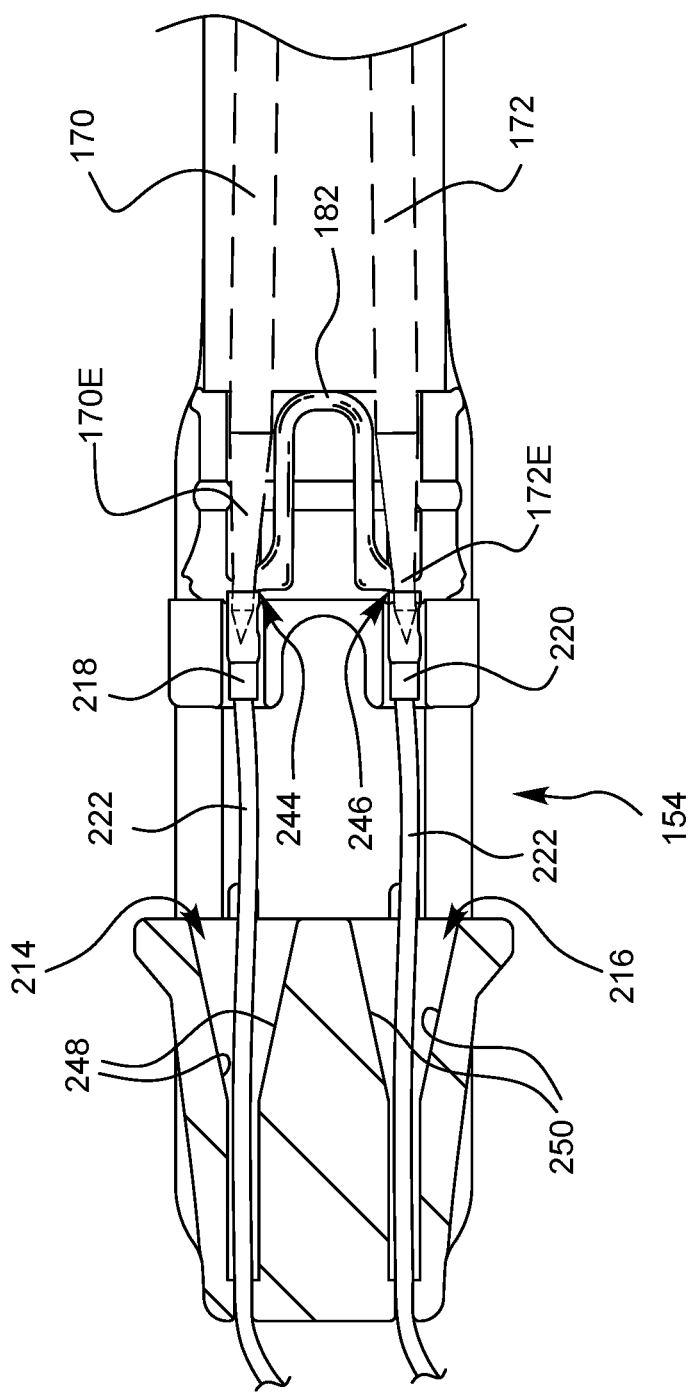
FIG. 10C is an enlarged partial cross-sectional view of the guide tip from FIG. 10B, showing the ferrules coupled to the needles being held distally to the ferrule removal spring.

FIG. 10B is a partially cross-sectioned side view of the prosthetic suturing device 150 of FIG. 1B, with the needles 170, 172 fully retracted. FIG. 10A is a top view of the device from FIG. 10B, hiding the handle, housing, spring, and hard stop in order to more clearly show the proximal needle orientation. The position of the needles 170, 172 in FIG. 10B is the position the needles 170, 172 take when the user is not applying force to the handle 160. FIG. 10C is an enlarged partial cross-sectional view of the guide tip 152 from FIG. 10B, showing the ferrules 218, 220 coupled to the ends of the needles 170E, 172E being held distally to the ferrule removal spring 182. The ferrule removal spring 182 has a first edge 244 which rides on the first needle 170 and which is positioned to push the ferrule 218 off of the first needle 170 if the needle 170 is moved more in a proximal direction. The ferrule removal spring 182 also has a second edge 246 which rides the second needle 172 and which is positioned to push the ferrule 220 off of the second needle 172 if the needle 172 is moved more in a proximal direction. As it stands in the view of FIG. 10C, however, the ferrules 218, 220 are still coupled to their respective needle ends 170E, 172E. The suture 222 has been pulled through the cuff receiving area 154 on a path where the needles 170, 172 had been pulled back. As will be shown and described in later figures, if there had been a sewing cuff located in the cuff receiving area, the suture 222 would have been pulled back through the sewing cuff in two locations (where the first and second needles 170, 172 had passed).

The view of FIG. 10C also offers a cross-sectional look at the first and second ferrule receiving apertures 214, 216. The flared end 248 of the first ferrule receiving aperture 214 and the flared end 250 of the second ferrule receiving aperture 216 can be seen more clearly in this view.

Figure 11C:
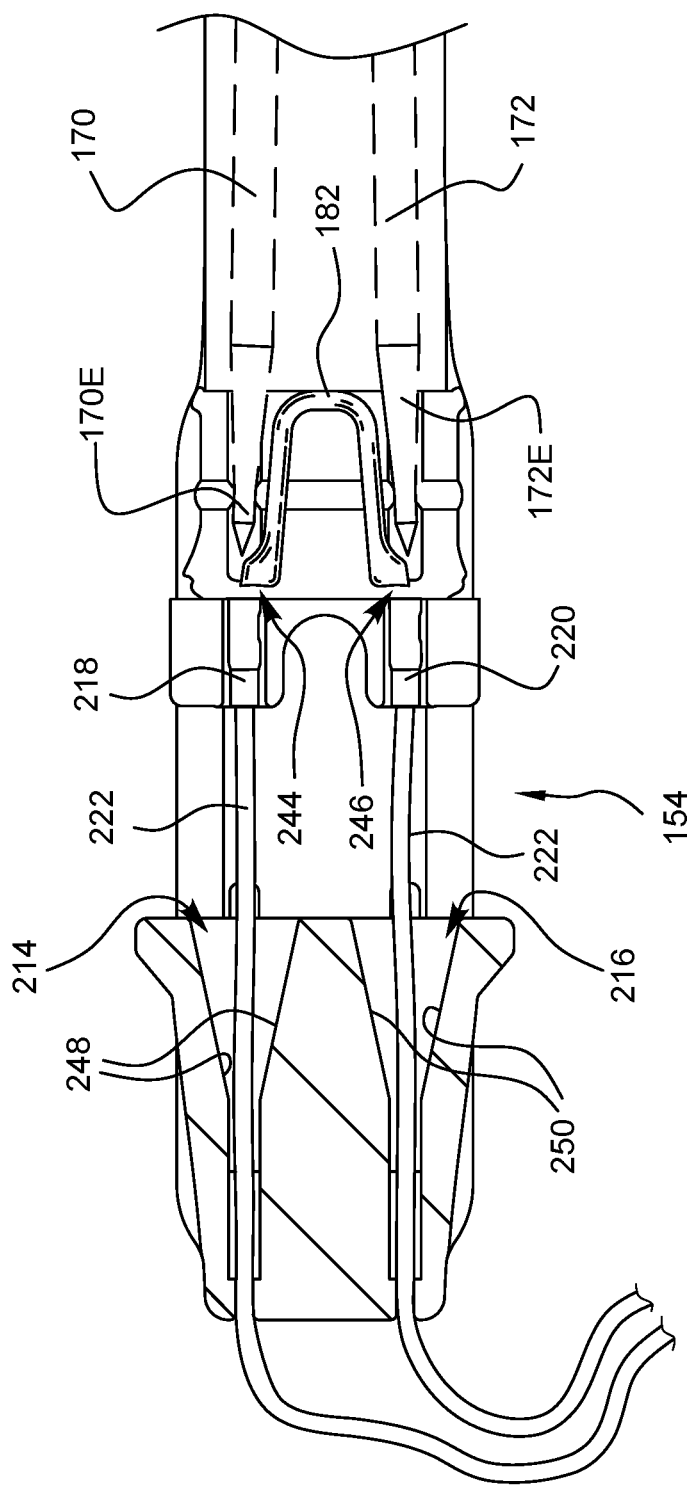
FIG. 11C is an enlarged partial cross-sectional view of the guide tip from FIG. 11B, showing the ferrules decoupled from the needles after having been removed from the needles by the ferrule removal spring.

FIG. 11B is a partially cross-sectioned side view of the prosthetic suturing device 150 of FIG. 1B, with the needles 170, 172 hyper-retracted. FIG. 11A is a top view of the device from FIG. 11B, hiding the handle, housing, spring, and hard stop in order to more clearly show the proximal needle orientation. In FIG. 11B, the user has applied a force to the handle 160 in a direction away 242 from the grip 175. The handle 160 may contact the handle stop 166 which can be designed to flex or give in order to allow the handle to move in this direction 242. This causes the needles 170, 172 to retract more than the normal resting state of FIG. 10B in a proximal direction 240. FIG. 11C is an enlarged partial cross-sectional view of the guide tip 152 from FIG. 11B, showing what happens when the needles 170, 172 are hyper-retracted in this fashion. The ferrules 218, 220 are decoupled from the ends of the needles 170E, 172E after having been pushed off of the needles 170E, 172E by the ferrule removal spring 182. This allows the suture to be removed from the device 150, and a new set of ferrules may be loaded into the device. This can be helpful in a cardiac surgery where there are often many pairs of suture ends which have been sewn into tissue and which then have to be sewn into corresponding positions in a sewing cuff of a replacement anatomical structure.

Figure 12:
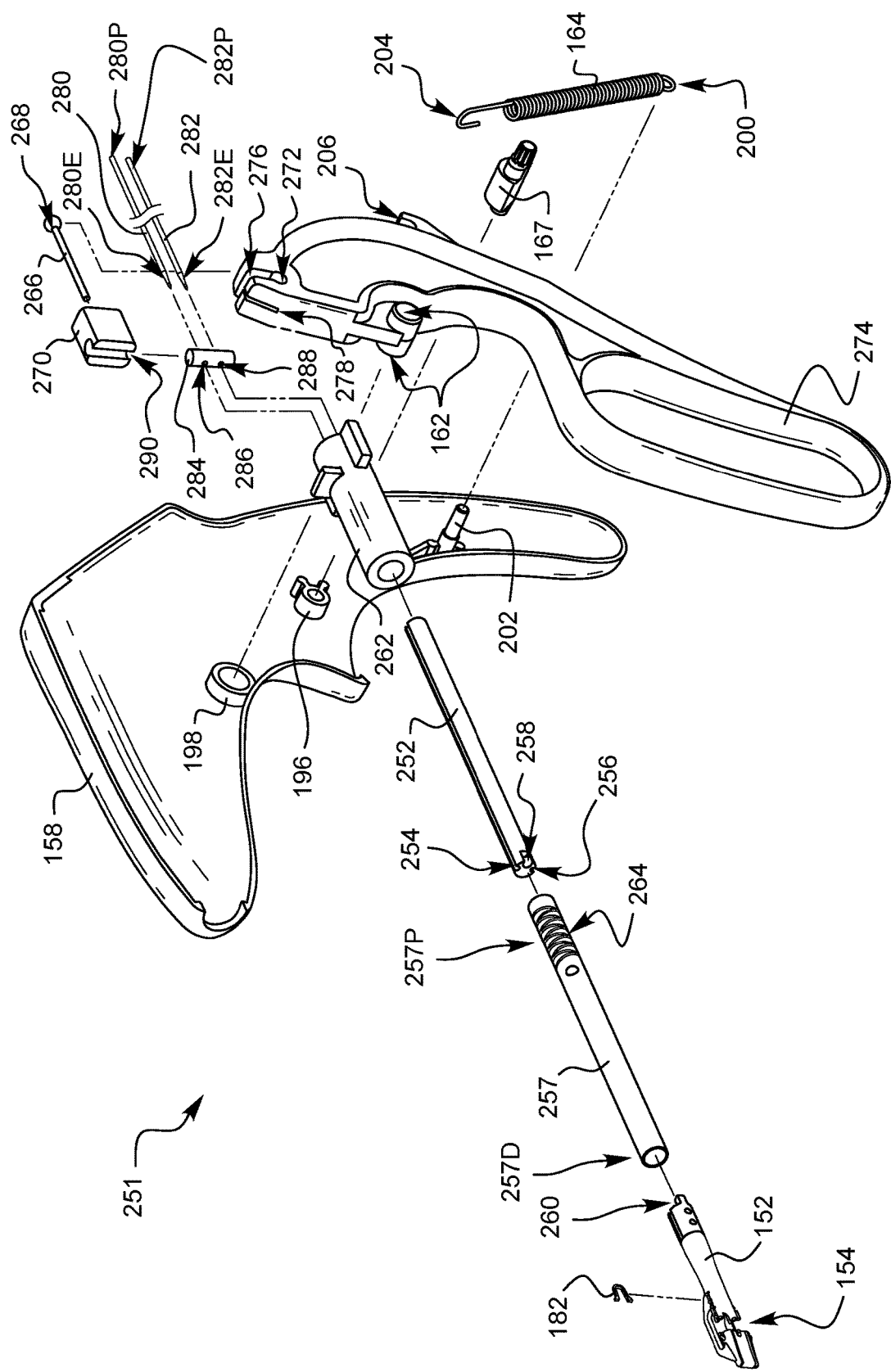
FIG. 12 is an exploded perspective view of another embodiment of a prosthetic suturing device.

FIG. 12 is an exploded perspective view of another embodiment of a prosthetic suturing device 251. The main difference between this embodiment and the previous embodiments is that the needles retain a vertical alignment throughout, rather than starting in a horizontal alignment and then being twisted into a vertical alignment. A needle guide tube 252, this one having a first straight track 254 and a second straight track 256, is placed into a proximal end 257P of shaft 257. A guide tip 152 is placed into a distal end 257D of the shaft 257, and a notch 258 of the needle guide tube 252 is aligned with a key 260 of the guide tip 152 inside of the shaft 257. A shaft holder 262 is coupled to grooves 264 of the shaft 257.

A drive rod 266 has a ball end 268 on a proximal end of the drive rod 266. The distal end of the drive rod 266 is coupled to a drive block 270. The ball end 268 of the drive rod 266 is placed into a side opening 272 in the handle 274, while the drive rod is pulled across a top slot 276 and down a forward slot 278 in the handle. A first needle 280 has an end 280E configured to engage a suture adapter, such as a ferrule. The first needle 280 also has a proximal needle end 280P. A second needle 282 has an end 282E configured to engage a suture adapter such as a ferrule. The second needle 282 also has a proximal needle end 282P. The second needle 282 is placed into the second straight track 256 of the needle guide tube 252, end 282E first. The ferrule release spring 182 may be placed into a slot in the top of the guide tip 152 and rested on the second needle 282. The first needle 280 may then be placed into the first straight track 254 of the needle guide tube 252, end 280E first, so that the spring 182 is compressed between the two needles 280, 282 as in previous embodiments.

A needle connector 284 has first and second connector holes 286, 288 into which the proximal ends of the first and second needles 280P, 282P are placed, such that the proximal ends 280P, 282P are coupled to their respective connector holes 286, 288. The needle connector 284 is coupled to a connector receptacle 290 in the drive block 270, completing the link between the needles 280, 282 and the handle 274.

The pivot point 162 of the handle 274 may be aligned in a pivot boss 198 formed in the housing 158. The shaft holder 262 may be held and supported by a variety of features on the inside of the housing 158. Such features are not illustrated for simplicity, but are well known to those skilled in the art. Although only one half of the housing 158 is shown in this exploded view, it should be understood that a complementary half of the housing is also present (though not shown) and would have similar boss features to allow pivoting of the handle 274 and bracing of the shaft holder 262.

The hard stop 167 may be mounted in a hard stop boss 196 to limit travel of the handle 274, while a lower end 200 of spring 164 may be coupled to a fixed spring attachment point 202 on the housing. An upper end 204 of the spring 164 may be hooked onto a handle spring attachment point 206.

Figure 13:
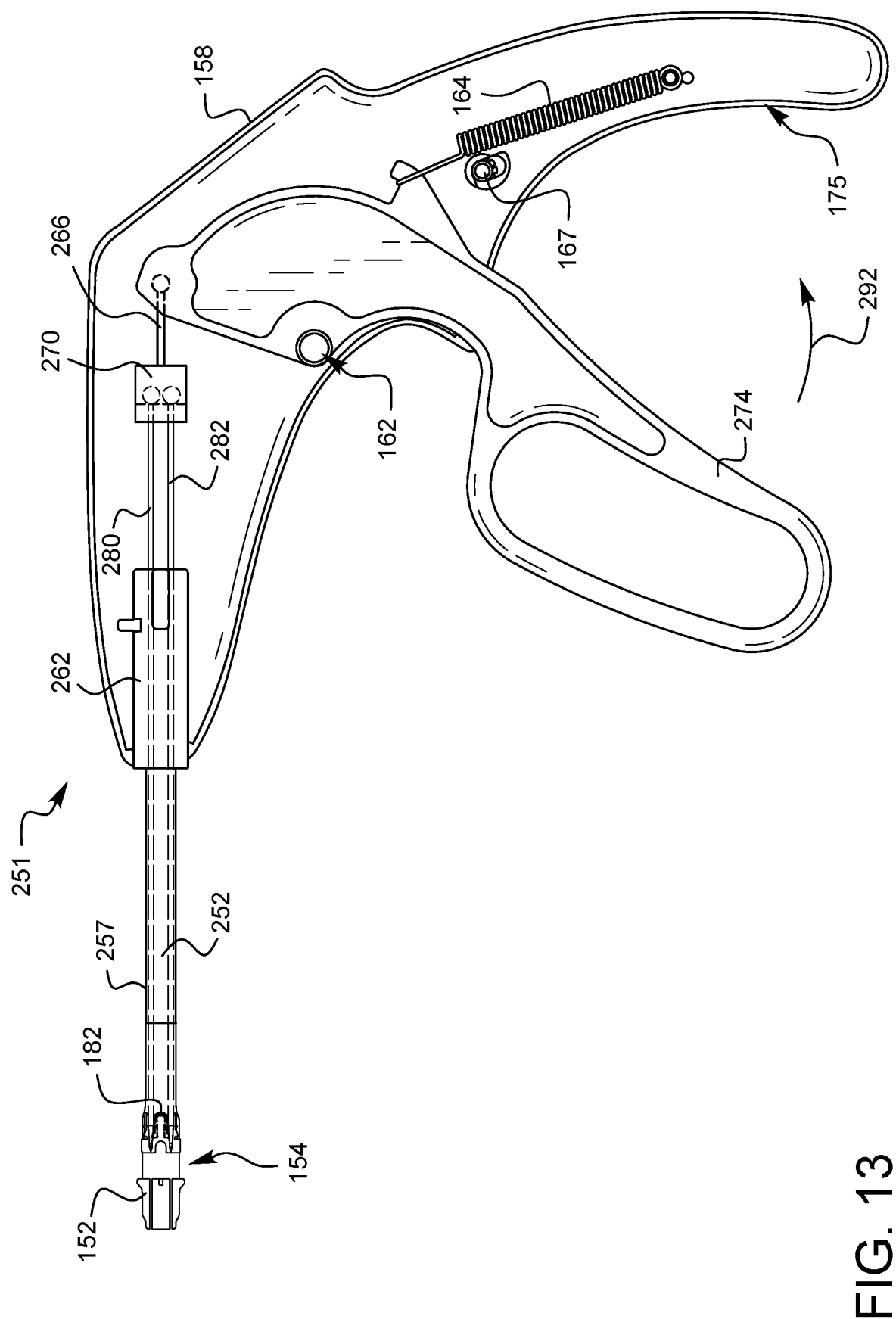
FIG. 13 is a partially exposed side view of the prosthetic suturing device of FIG. 12.

FIG. 13 is a partially exposed side view of the prosthetic suturing device 251 of FIG. 12. When the handle 274 is squeezed 292 towards the grip 175, the first and second needles 280, 282 are moved distally through the cuff receiving area 154 in a manner as shown in the previous embodiments.

Figure 14:
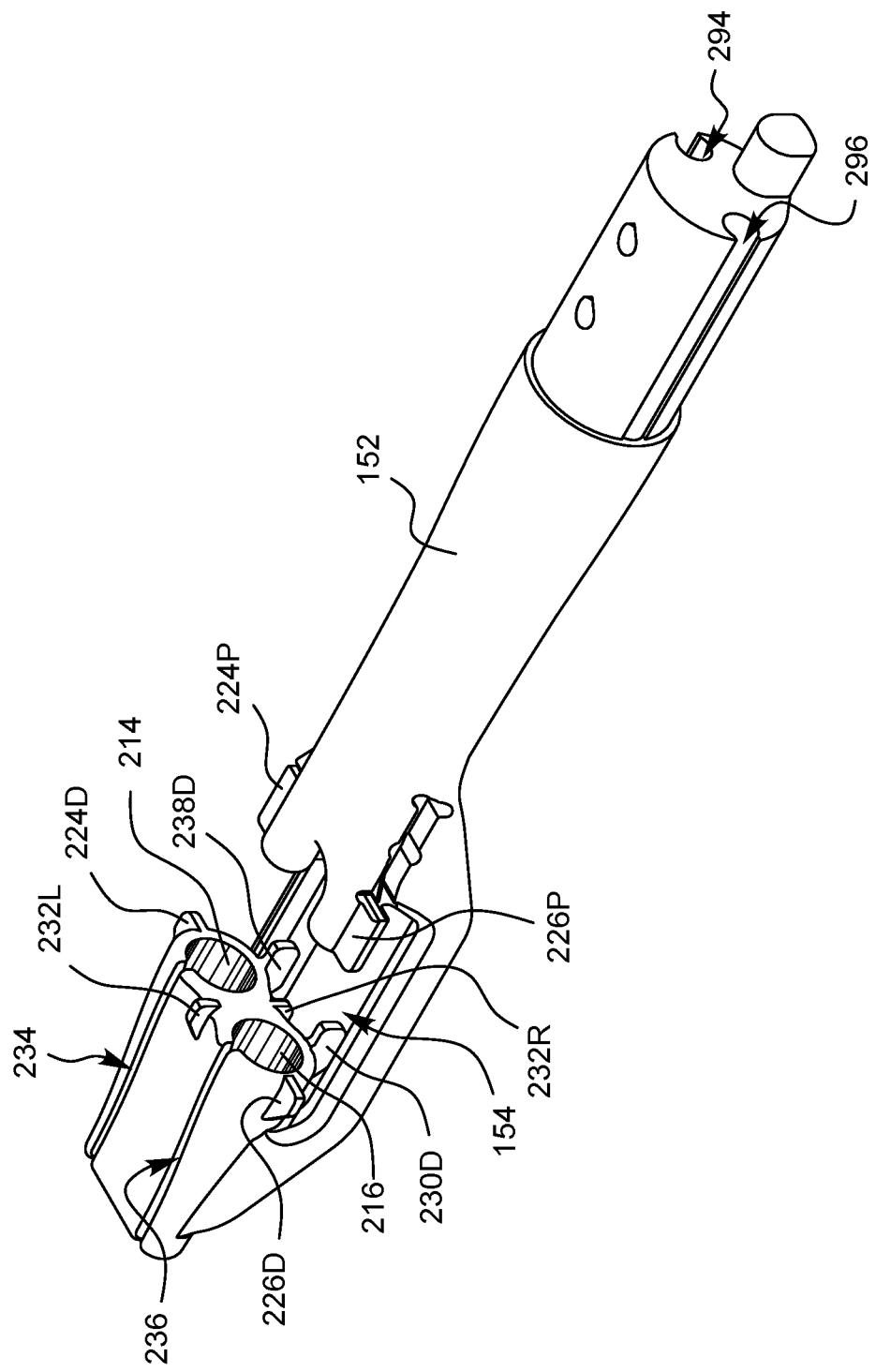
FIG. 14 is a perspective view of one embodiment of a guide tip for a prosthetic suturing device.

FIG. 14 is a perspective view of one embodiment of a guide tip 152 for a prosthetic suturing device. Most features of this embodiment of a guide tip 152 have been discussed above, however, this embodiment can also be seen to have first and second proximal needle guides 294, 296. These guides 294, 296 work with the needle guides 210, 212 (not visible in this view, but discussed previously) in order to help guide the needles 280, 282 through the cuff receiving area while maintaining an expected vertical alignment and spacing between the needles 280, 282.

Figure 15:
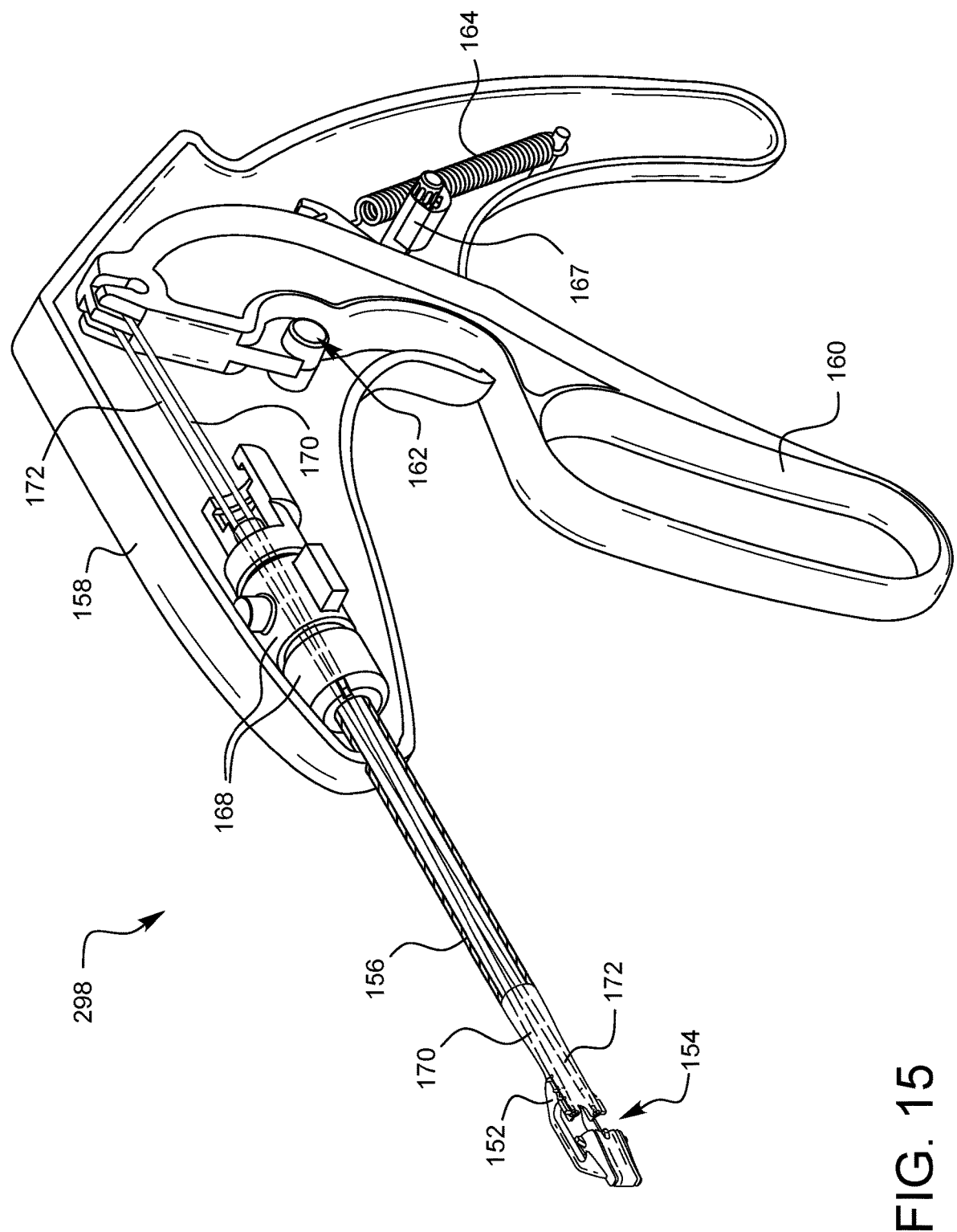
FIG. 15 is a partially exposed partial cross-sectional perspective view of another embodiment of a prosthetic suturing device, utilizing the guide tip of FIG. 14 without a needle guide tube.

Depending on the embodiment, the needle guides 294, 296 in the guide tip 152 may be used to force needles which start horizontally into a vertical alignment without the need for a needle guide tube. FIG. 15 illustrates just such an embodiment, and is a partially exposed partial cross-sectional perspective view of another embodiment of a prosthetic suturing device 298, utilizing the guide tip of FIG. 14 without a needle guide tube. The features of this embodiment are just like those of the embodiment of FIG. 1B, however, this device 298 does not use the a needle guide tube. Instead, the needles 170, 172 start horizontally as held by the handle 160, but are then twisted into vertical orientation by the guide tip 152. In order to prevent the needles from buckling, it may be necessary to go with a heavier gauge needle when a suture guide tube is not used.

Figure 16:
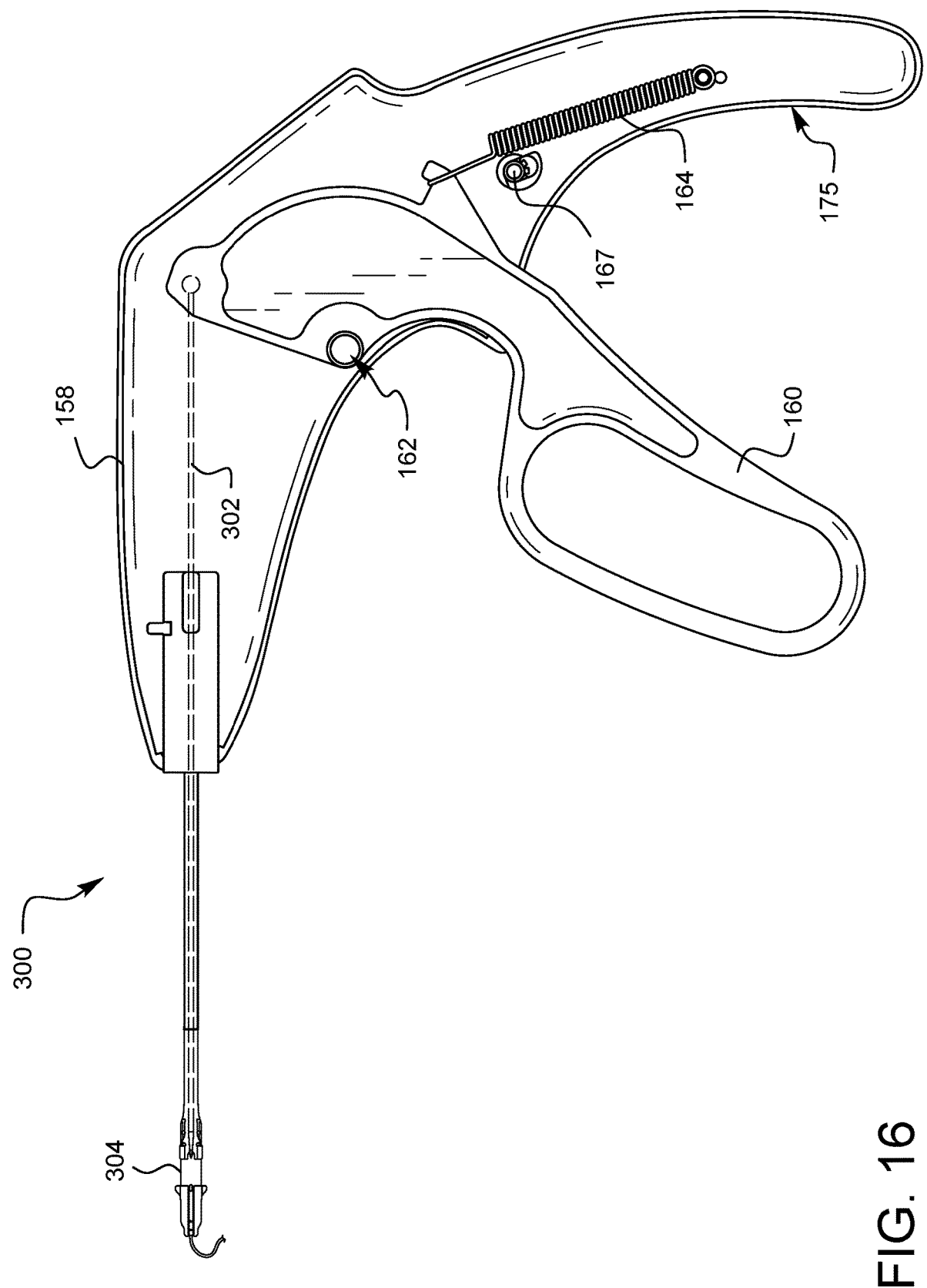
FIG. 16 is a partially exposed side view of a further embodiment of a prosthetic suturing device.

FIG. 16 is a partially exposed side view of a further embodiment of a prosthetic suturing device 300. This embodiment only has a single needle 302 and a place for a corresponding ferrule holder in the guide tip 304, but the cuff receiving area is still facing left while the handle 160 and grip 175 substantially point down (as in previous embodiments).

Figure 17:
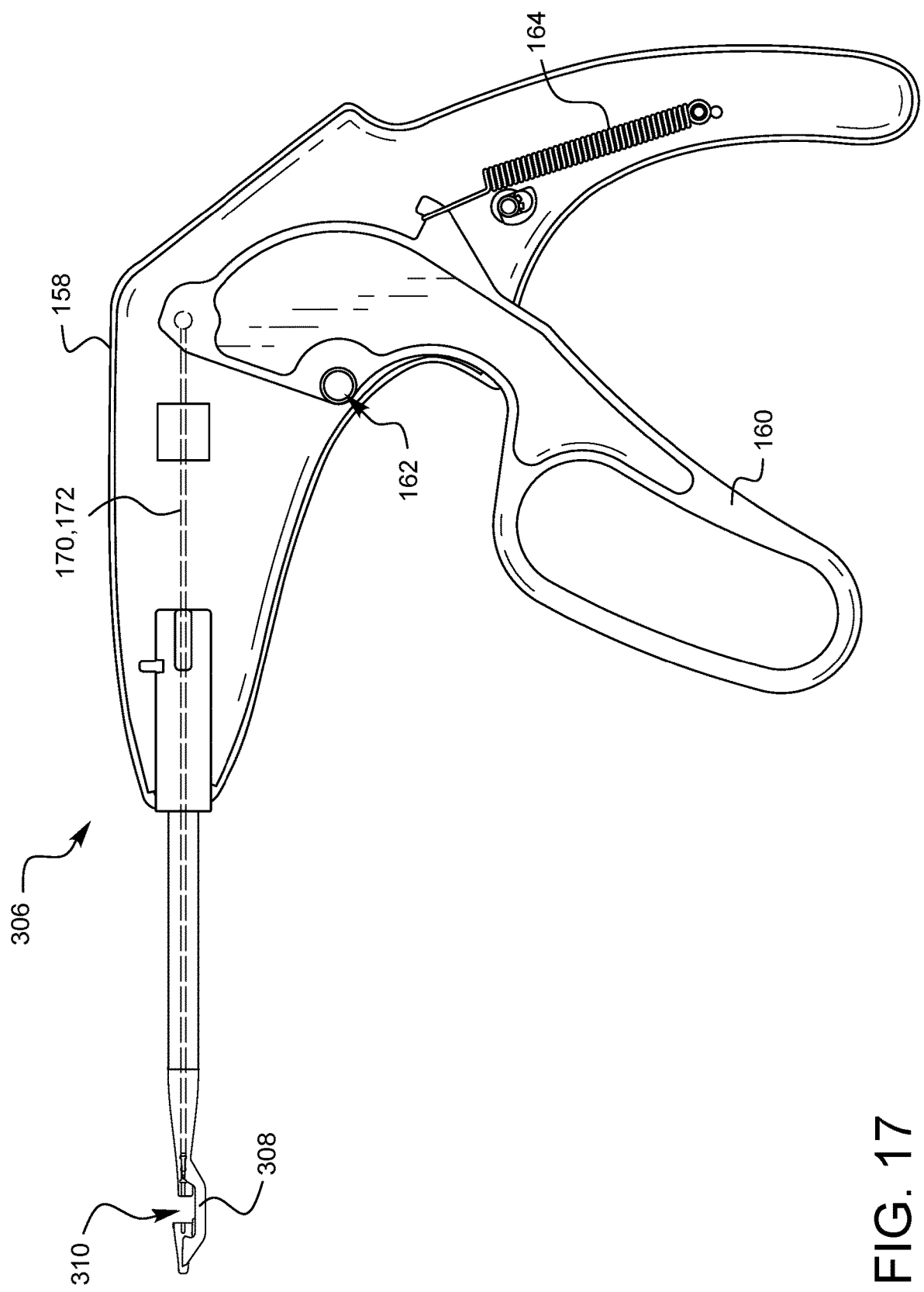
FIG. 17 is a partially exposed side view of another embodiment of a prosthetic suturing device.

FIG. 17 is a partially exposed side view of another embodiment of a prosthetic suturing device 306. In this embodiment, the guide tip 308 has a vertical opening (rather than a horizontal opening like previous embodiments) which defines a cuff receiving area. The needles 170, 172 in this embodiment are aligned horizontally, and otherwise, this device operates like the previous embodiments.

Figure 18B:
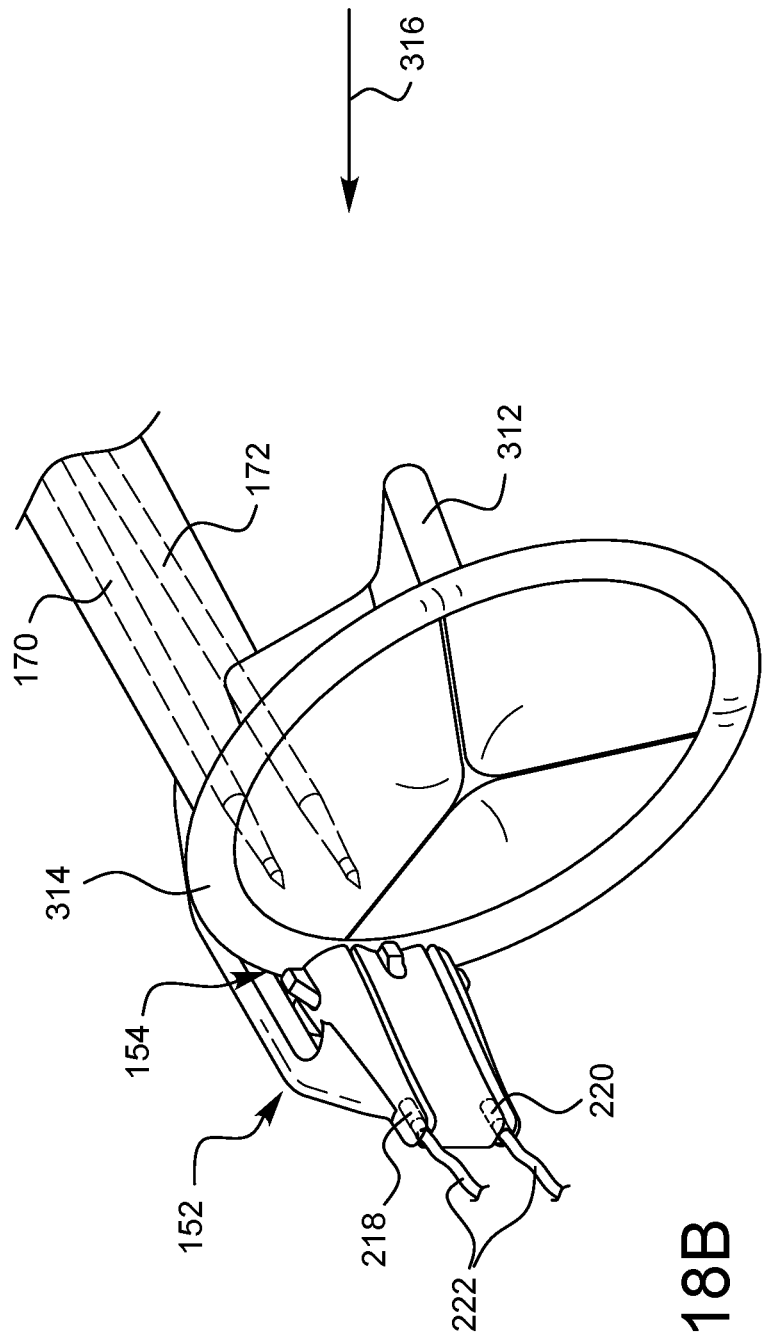

FIGS. 18A-18F illustrate one example of a surgical usage of an embodiment of a prosthetic suturing device. For convenience, only the guide tip 152 of the device is shown in FIGS. 18A-18F. The guide tip 152 is like that of FIGS. 4 and 5, and as noted in the examples above, there are many actuator examples which would result in the vertically aligned needles 170, 172 illustrated here. The surgical situation of this example is as follows, and as illustrated in FIG. 18A: In preparation for installation of a replacement anatomical structure 312 (here, illustrated as a replacement heart valve), a suture 222 has been sewn through a tissue 315 inside of a patient. This could have been done by hand, but preferably with a minimally invasive suturing device which is compatible with ferrules (or some other type of suture adapter). The ferrules 218, 220 were removed from the minimally invasive suturing device and then loaded into the ferrule holders in the distal end of the guide tip 152 outside of the patient. The replacement anatomical structure 312, having a sewing cuff 314, is standing by.

Figure 18C:
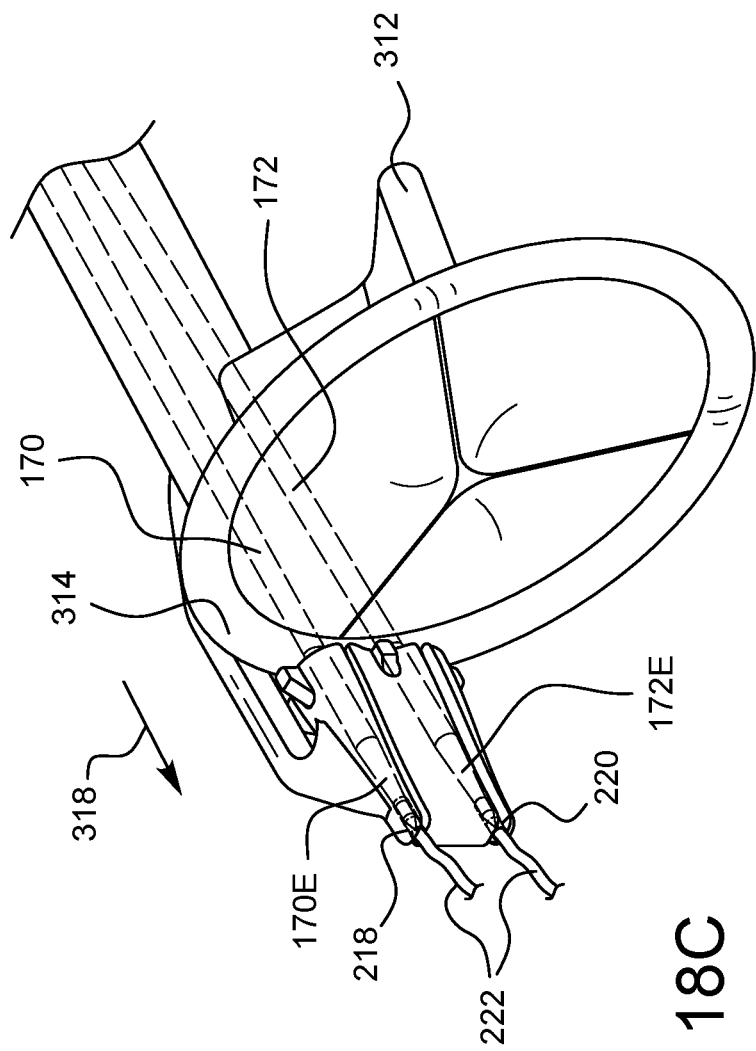
Figure 18D:
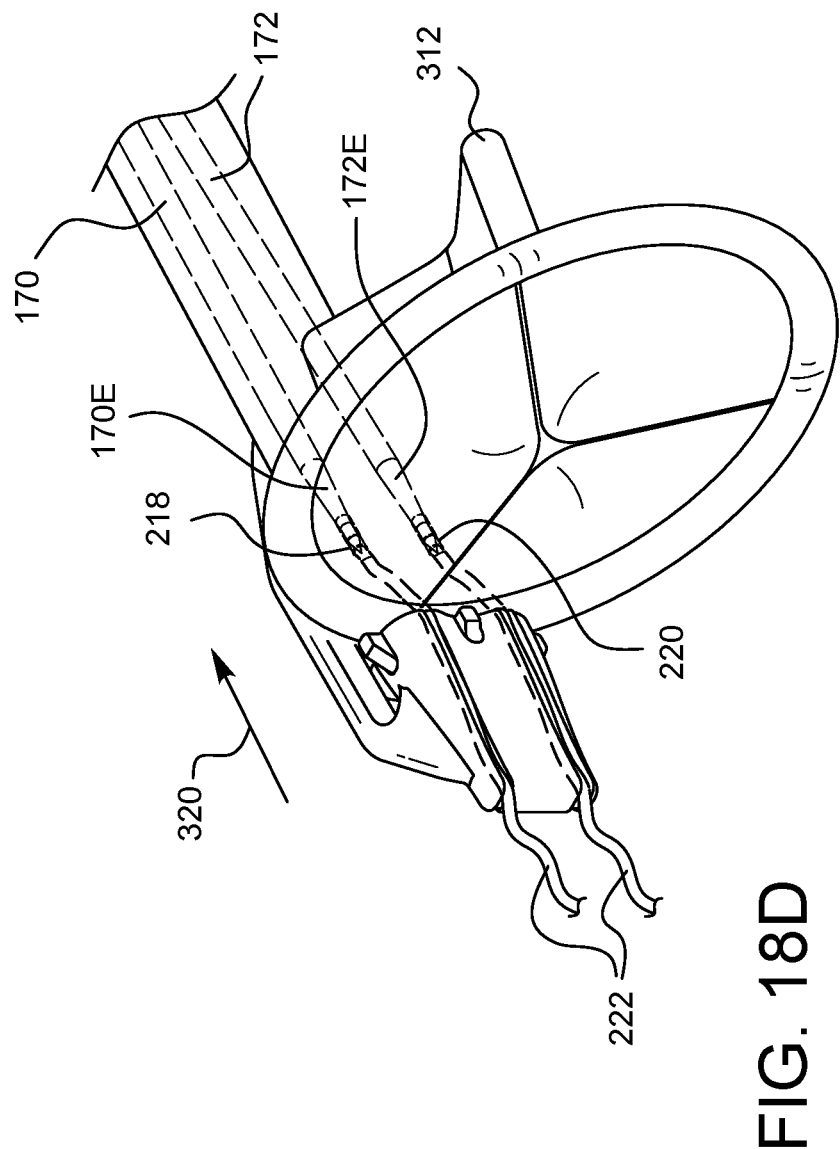
Figure 18E:
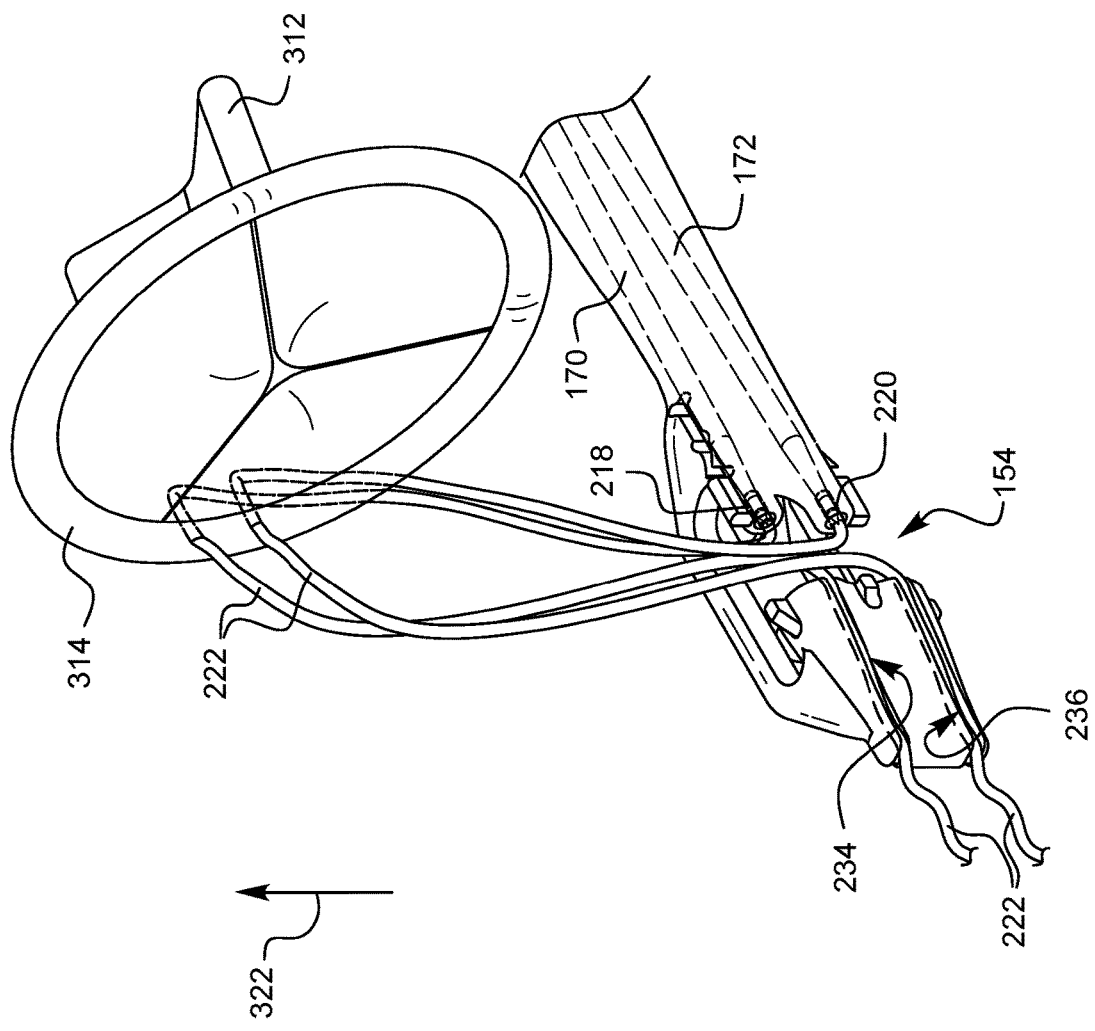
Figure 18F:
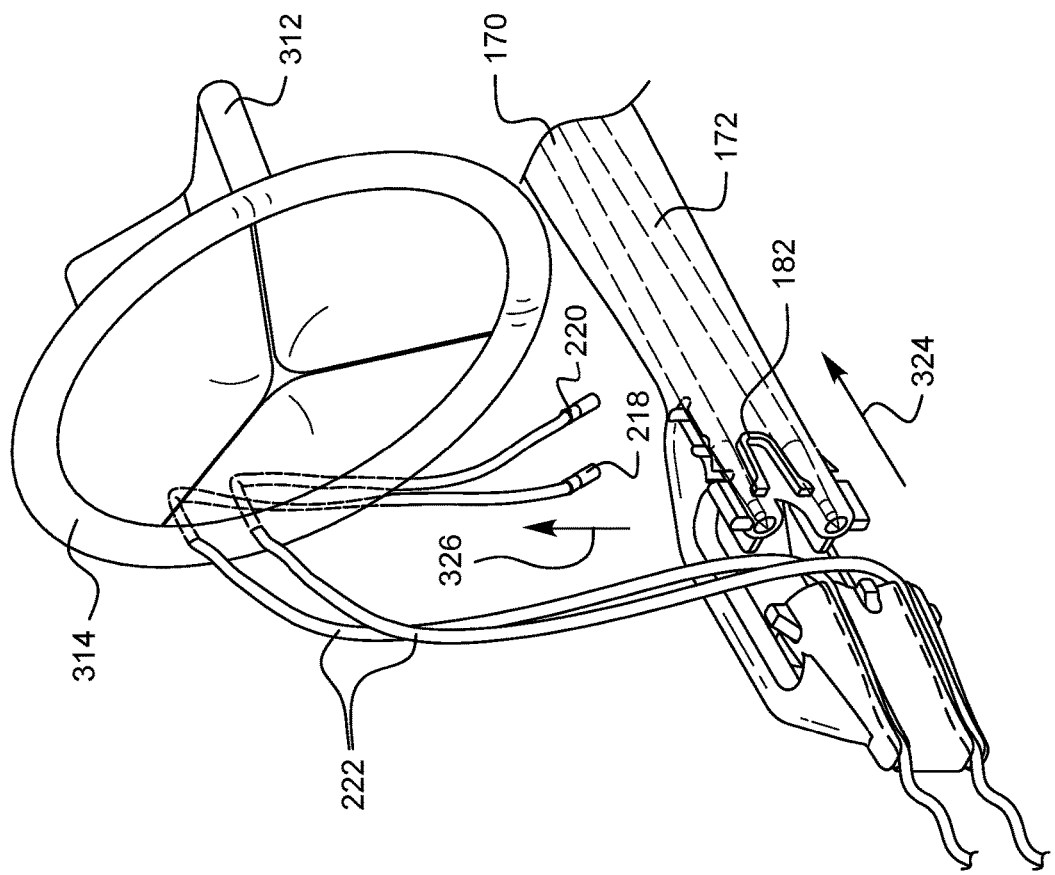

As shown in FIG. 18B, the sewing cuff 314 of the replacement valve 312 is placed 316 into the cuff receiving area 154 of the guide tip 152. As described previously, the needle alignment guides can be used to help position the sewing cuff as desired. Since the cuff receiving area faces to the side, while the handle and grip face substantially downward, it is easier for a surgeon to hold the suturing device with one hand while positioning the valve 312 with the other hand. As shown in FIG. 18C, the device handle (not shown) is squeezed to cause the needles 170, 172 to move distally 318, pierce the sewing cuff 314, and then engage the ferrules 218, 220 with respective ends 170E, 172E of the needles 170, 172. As shown in 18D, the device handle (not shown) is released to cause the needle ends 170E, 172E to move proximally 320 back through the sewing cuff 314, pulling the ferrules 218, 220 and the suture 222 back through the sewing cuff as well. As shown in FIG. 18E, the replacement anatomical structure 312 can be removed 322 from the from the cuff receiving area 154 while the ferrules 218, 220 remain coupled to the needles 170, 172 in the proximal end of the guide tip 152. Although the suture 222 is still illustrated as passing through the ferrule holders in the distal end of the device, it should be understood that the suture 222 can be removed from the ferrule holders by passing it through the suture removal passages 234, 236. As shown in FIG. 18F, the needles 170, 172 may be further moved in a proximal direction 324 (as discussed above) so that the ferrules 218, 220 are pushed off of the needles 170, 172 by the ferrule removal spring 182, thereby releasing the ferrules 218, 220 to move free 326 of the device. By loading other suture ends into the device, this process can be repeated with other suture pairs around the circumference of the sewing cuff 314. This device and method greatly simplify and speed up the process of placing sutures through a sewing cuff of a replacement anatomical structure. Once the desired number of suture ends have been passed through the sewing cuff, those skilled in the art know how to run the replacement anatomical structure down the sutures and against the tissue where the sutures were first placed. The pairs of suture ends may then be tied off with hand-tied or mechanical knots as desired.

Various advantages of a prosthetic suturing device have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A prosthetic suturing device, comprising:
   a guide tip defining a cuff receiving area, the guide tip comprising a first needle guide and a second needle guide;
   a shaft, whereby the guide tip is coupled to a distal end of the shaft;
   a housing coupled to a proximal end of the shaft, wherein the housing includes a grip comprising a back portion spaced from the distal end of the shaft, a grip left side portion and a grip right side portion, the grip left side portion and the grip right side portion extending from the back portion towards the distal end of the shaft and wherein the grip is configured to be held by a single hand, with a user's thumb on one of the grip left side portion and the grip right side portion, and wherein the cuff receiving area faces a side of the device that includes the one of the grip left side portion and the grip right side portion;
   a handle coupled to the housing and displaceable between a first position and a second position;

a first needle having a proximal end coupled to a portion of the handle, wherein the first needle guide of the guide tip is configured to guide a distal end of the first needle through the cuff receiving area, and wherein when the handle is displaced from the first position to the second position, the handle displaces the first needle between a retracted position in which the first needle is not passing through the cuff receiving area and an engaged position in which the first needle is passing through the cuff receiving area;

a second needle having a proximal end coupled to a portion of the handle, wherein the second needle guide of the guide tip is configured to guide a distal end of the second needle through the cuff receiving area, and wherein when the handle is displaced from the first position to the second position, the handle displaces the second needle between a retracted position in which the second needle is not passing through the cuff receiving area and an engaged position in which the second needle is passing through the cuff receiving area; and a needle guide tube having first and second spiral tracks, wherein at least a portion of the needle guide tube is disposed within the shaft, and wherein a portion of the first needle is disposed within the first spiral track and a portion of the second needle is disposed within the second spiral track such that (a) the proximal end of the first needle and the proximal end of the second needle are aligned in a first plane proximal to the needle guide tube and (b) the distal end of the first needle and the distal end of the second needle are aligned in a second plane distal to the needle guide tube, wherein the first plane is perpendicular to the second plane.

2. The prosthetic suturing device of claim 1, wherein the first needle includes a ferrule engaging end; and wherein the guide tip further comprises at least one ferrule receiving aperture.

3. The prosthetic suturing device of claim 2, wherein the at least one ferrule receiving aperture comprises a flared end facing the cuff receiving area.

4. The prosthetic suturing device of claim 3, wherein the flared end is configured to prevent a sewing cuff of a replacement anatomical structure from jamming in the at least one ferrule receiving aperture when the sewing cuff is pierced by the first needle when the first needle passes through the sewing cuff while passing through the cuff receiving area and into the transition needle guide.

5. The prosthetic suturing device of claim 1, wherein the grip points in a direction substantially orthogonal to the cuff receiving area.

6. The prosthetic suturing device of claim 1, further comprising a ferrule release spring disposed in a spring slot of the guide tip, the ferrule release spring having a first edge and a second edge, wherein the first edge rides along a portion of the distal end of the first needle and is configured to engage an end portion of a first ferrule disposed at the distal end of the first needle when the first needle is in the retraced position, and wherein the second edge rides along a portion of the distal end of the second needle and is configured to engage an end portion of a second ferrule disposed at the distal end of the second needle when the second needle is in the retraced position.

7. The prosthetic suturing device of claim 6, wherein the first plane is a horizontal plane and the second plane is a vertical plane.

8. The prosthetic suturing device of claim 6, wherein the ferrule release spring has a U-shape.

9. The prosthetic suturing device of claim 1, wherein a distal end of the needle guide tube abuts or lies close to a proximal portion of the guide tip inside the distal end of the shaft.

* * * * *